(12) United States Patent
Clements et al.

(10) Patent No.: US 6,946,253 B2
(45) Date of Patent: Sep. 20, 2005

(54) HERPES ZINC FINGER MOTIFS

(75) Inventors: John Barklie Clements, Glasgow (GB); Alasdair Roderick Maclean, Glasgow (GB)

(73) Assignee: University Court of the University of Glasgow (GB)

(*) Notice: Subject to any disclaimer, the term of this patent is extended or adjusted under 35 U.S.C. 154(b) by 0 days.

(21) Appl. No.: 10/332,795

(22) PCT Filed: Jul. 11, 2001

(86) PCT No.: PCT/GB01/03114

§ 371 (c)(1),
(2), (4) Date: Feb. 11, 2003

(87) PCT Pub. No.: WO02/04492

PCT Pub. Date: Jan. 17, 2002

(65) Prior Publication Data

US 2003/0186283 A1 Oct. 2, 2003

(30) Foreign Application Priority Data

Jul. 11, 2000 (GB) .............................. 0016890

(51) Int. Cl.[7] .............................................. C12Q 1/68
(52) U.S. Cl. ........................... 435/6; 435/7.1; 435/69.1; 435/7.93
(58) Field of Search ........................... 435/6, 7.1, 69.1, 435/7.93

(56) References Cited

U.S. PATENT DOCUMENTS

| 5,585,367 A | 12/1996 | Vandevelde et al. |
| 5,767,135 A | 6/1998 | Fernandez-Pol ............. 514/354 |
| 5,874,094 A | 2/1999 | Costello ...................... 424/401 |

FOREIGN PATENT DOCUMENTS

| EP | 0 524 961 | 7/1994 | |
| WO | WO 98/54311 | 12/1998 | ........... C12N/15/01 |

OTHER PUBLICATIONS

Ingram et al, Journal of General Virology, 1996, vol. 77, 1874–1851.*

Beerheide et al. "Potential Drugs Against Cervical Cancer: Zinc–Ejecting Inhibitors of the Human Papillomavirus Type 16 E6 Oncoprotein" *Journal of the National Cancer Institute* 91(14): 1211–1220 (1999).

Communication Pursuant to Article 115(2) EPC for European Application No. EP–A–1299725 submitted on Feb. 14, 2005.

Gaudin et al. "Conformational Flexibility and Polymerization of Vesicular Stomatitis Virus Matrix Protein" *Journal of Molecular Biology* 274(5): 816–825 (1997).

Maynard et al "Reativity of the HIV–1 Nucleocapsid Protein p7 Zinc Finger Domains from the Perspective of Density-Functional Theory" *Proc Natl Acad Sci USA* 95: 11578–11583 (1998).

Rice et al "Azodicarbonamide Inhibits HIV–1 Replication by Targeting the Nucleocapsid Protein" *Future Medicine* 3(3): 341–345 (1997).

Vandeleve et al. "Letter to the Editor: ADA, A Potential Anti–HIV Drug" *AIDS Research and Human Retroviruses* 12(7): 567–568 (1996).

Zhi et al. "Self–Interaction of the Herpes Simplex Virus Type 1 Regulatory Protein ICP27" *Virology* 257(2): 341–351 (1999).

Colasanti M. et al. "S–nitrosylation of viral proteins: molecular bases for antiviral effect of nitric oxide" *International Union of Biochemistry and Molecular Biology* 48(1):25–31 (Jul. 1998) Abstract Only.

International Search Report corresponding to PCT GB01–03114 mailed on Mar. 11, 2002.

* cited by examiner

*Primary Examiner*—Ali R. Salimi
(74) *Attorney, Agent, or Firm*—Myers Bigel Sibley & Sajovec

(57) ABSTRACT

The present invention relates to a method for detecting an agent for use in the treatment of herpes virus infection and use of known agents, such as 2,2'-dithiobisbenzamide (DIBA) and azodicarbonamide (ADA), and unknown agents, which selectively eject zinc bound to a zinc finger protein, for the manufacture of a medicament for the treatment of herpesvirus infections.

17 Claims, 7 Drawing Sheets

FIGURE 1: AMINO ACID CONSERVATION OF IE63 AND HOMOLOGUES

Figure 3:
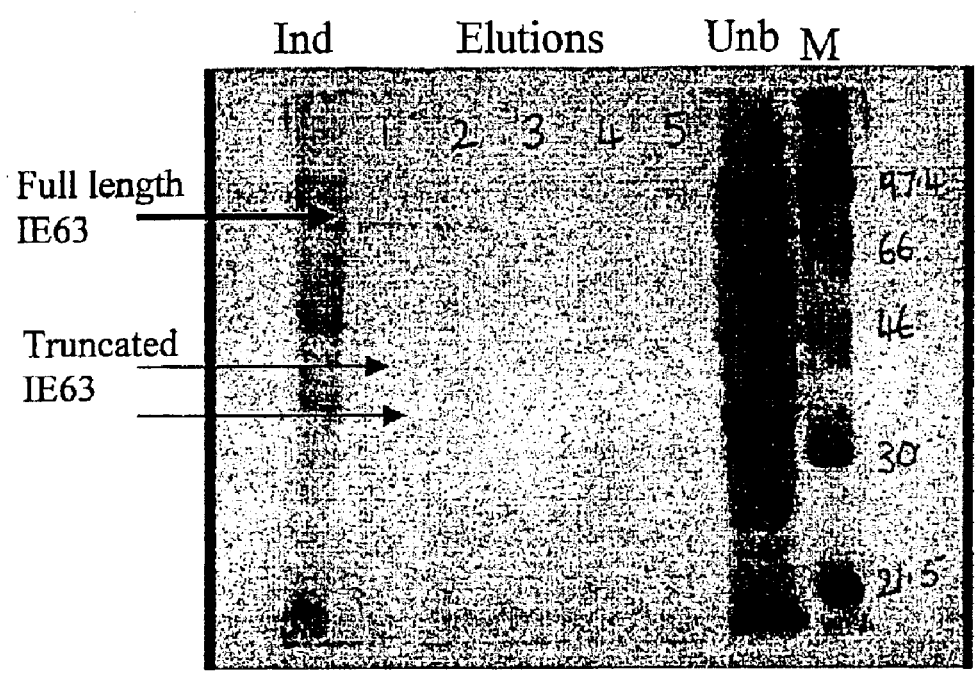

```
Alphaherpesviruses

HSV-1    MATDIDMLIDLGLDLSDSDLDEDPPE.PAESRRDDLESDSSGECSSSDEDMEDPHGEDGPEFILDAARPAVRPSRPEDPG
HSV-2    MATDIDMLIDLGLDLSDSELEEDALERDEEGRRDDPESDSSGECSSBDEDMEDPCGDGGAEAI.DAAIPKGPPARPEDAG
EHV-1                             MALSSVSSCEPMEDEMSIMGSDTEDNFTGGDTCA
EHV-4                             MALSSVSSCEPMDDEMSIMGSDTDDTL.GGSCVE
BHV-1                             MADPEIATLSTASESDDLSLFGSDRE
PRV
VZV                                                                          MASASIPTD
MDV                               MSVDAFSRESDDMMSLLDYDFIEGSSSDENAEVTEMETSAK

HSV-1    VPSTQTPRPTBRQGPNDPQPAPHSVWSRLGARRPSCSPEQHGGKVARLQPPPTKAQPARGGRRGRRRGRGRGGPGAADGL
HSV-2    TPEASTPRPAARRGADDPPPATTGVWSRLGTRRSASPREPHGGKVARIQPPSTKAPHPRGGRRGRRRGRGRYGPGGADST
EHV-1    BATRGLVNKSAPVPTQTVGTVSALRNVVGDPPKSVVVSPSASPQRAQPSNPKSERPAPGHGRRNRRAPPFRRNNWKQQQRG
EHV-4    AAQSAVVNKRAFEMSEGTOTMSTIRNVVSEVPKSLVVSPAASPKNPKPQNTTSERSAFPHCRKNRRRPFRRNNWK..QRA
BHV-1    PDDEAPSLAPALRSVVGQVRKRKLEGAEDEPMPAEPPGEGAASGDKGPAEAPPARRRARVRPRRPRRRPRRRQPAGPQRSR
PRV             MEDSGNSSGSEASRSGSBERRPVRERLGSRPPBRRPVRARLGAIRRRRGGRGGRAARQALRQRRBQQQQQRQQQHQR
VZV      PDVSTICEDFNNLLPDEPSDDFALEVTDWANDEAIGSTPGEDSTTSRTVYVERTADTAYNPRYSKRRHGRRESYHHNRPK
MDV      TANNKNEVLPAPPCTQELLTERPSPDSKNSQGDDDSNSIYGNVIRDAQHSASRYATRCLDNAIPRKRLRLANLTVDSACI

HSV-1    SDPRRRADRTTRNPGGPRPCAGWTDCPGAFHGEAWRGSEQPDPPGGQRTRGVRQAPPPLMTLAIAPPPADPRAPADERKA
HSV-2    PKPRRRVSPNAHHNQGGRHPASARTDGPGATHCEARRGGEQLDVSGGPRPRGTROAPPPLMALSLTPPPHADGRAPVPPRKA
EHV-1    WEKPEPENVPARQSAGSNPKRSSLPVHMRLGQRPGGDSSSADSGHGGAGPSDRWRFKTRTQSVARVHRNRRRGNANHGSNT
EHV-4    WEKQSQEAAPANQGSRNWPKRSSMPVHMRLGHRSGDFQSADAGHCTAGPSGGWRFKTRTHSASRVYHNRQRGNTNKSGNA
BHV-1    GPAAKREAALATSHGGGGAAARSIGSSLRLARSLAEAAQ RATAERVTAVFAGARLDLMRPVQNGGFRAAGV.......
PRV      RRQEADRPDGGPD APPDRLSESARAAVSATHA RVGATRVNELFASARIDLSRPVFNDGFRAAGS..............
VZV      TLVVVLPDSNIHHGGRDVSTGYARIERGHRRSSRSYNTQSSRRKRDRSLSNRRRRPTTPPAMTTGERNDQTHDESYRLRPS
MDV      SQTKBPHCTCNRKQYHRRNPPMSDTSQEKIHLRLHNRLGSRSBKQQRSLNYDRRLQEGHHRRRFYSERRIYDQNHSHHRT

HSV-1    PAADTIDATTRLVLRSISERAAVDRISESFGRSAQVMHDPFGCGQPPPAAN.........SPWAPVLAGQGG.PFPDAETR
HSV-2    PSADTIDPAVRAVLRBISERAAVERISESFGRSALVMQDPPGGMPFPAAN.........SDWAPVLATQAG.GFDAETR
EHV-1    .PGRSAGDRLWAAAASSIADVCRRVTSSRIGBMFHGARETLTTPVIQKGGFRAENS......SPWAFVLGFGSD.QFNPEAR
EHV-4    SSSRSGDRLWAAAANAIXDVSKRVTSSRISDMFHGARETLTSPVWQGCPRABHS......SPWSFVLSFGLS.QFNPEGR
BHV-1    ..................................................SPWAAVLDFGAE.QFVPEGR
PRV      ..................................................SPWAAVLEFGAE.QFTPDGR
VZV      KRDARRSRIRKEYDTPVDRITGRAIEVVSTAGASVTIDSVRHLDETIEKLVVRYATIQEGDSWASGGCPPGI......KQ
MDV      HDIRVPLEKYRVSRQHDLFVHEELNEILQREKHRLASISNECDYRVSSK...........NRHWAAVLTFSSHAESTLCGP

HSV-1    RVSWETLVAHGPSLYRTFAGNPRAASTAKAMRDCVLRQENFIEALABADETLAWCEMCIHHNLPLRPQDPIIGTTAAVLD
HSV-2    RVSHETLVARGPSLYRTBAANPRAASTAKAMRDCVLRQENLIPALABADETLAWCKMCIHHNLFLRPQDPIIGTAAAVLE
EHV-1    RITWDTLVEBGVNLYKLFEVRSHAAEAARSLRDAVMRGENLLEALABADETLSWCENIVTKQLFMRTRDPIISSSVALLD
EHV-4    RITWDTLVTHGENLYKLFEVRSHAAEAARSLRDLVMRGENLLEALASADETISWCKMIITKNLPMRTRDPIIHSSIALLR
BHV-1    RVTNETLMFHGRDLYRMFEVRPHAAQAAPALRDLVLRSANLVDALASADECLTWCEPIATKNLRLRTKDPIVATAGAVLE
PRV      RVTWRTLMFHGADLHRLFEVRPHATEAARVLREMVLDEGLTESLABADETLTNVKLILITKGLTLRTLDPIVATAGAVLQ
VZV      NTSWPELMLYGHELYRTPESYKMDSRIARALRERVIRGESLIEALESADELLTWIKMLAAIQNLPIYTNNPIVATSKSLLE
MDV      QITWEYLLHAGPELRNTFEIRPRISLQASAAREAVLRGESFIAALGSAEETLSWLKLHAVLKLRLVNHDPIFKTAGAVLD

HSV-1    NLATRLRPPLQCYLKAR....GLCGLDELCSRRRLADIKDIASFVFVILARLANRVERGVAEIDYATLGVGVCBKMHYYL
HSV-2    NLATRLRPFLQCYLKAR....GLCGLDDLCSRBRLSDILASFVLVILARLANRVERGVSEIDYTTVGVGAGETMHYYI
EHV-1    NLRLKLEPPFMRCYISSS....GSPTLAELCDHQRLSDVACVPTFMPVMLARIARAVGSGABTVSRDALGPD.CRVLADYV
EHV-4    NLRLKLEPPFMRCYLSSS....GSPTLAELCDHQRLSDVACVPTFMFVTLARIARAVGSGAEAVSPDALGPA.GHALANYV
BHV-1    NLRLKLAPPFLRCYLRGR....GLPSLEELCAARRLSLATCPASYMFVMLARLSRAVRSGAECVPLLEVTVG.DAPFSEYI
PRV      NLRLKLGPPFLRCYLRDT.......PVDELVRRRRRLRDVRCIVTYTLVMLARIARVVERGSSCVLPPDLGDS.PVPLEEYV
VZV      NLKLKLGPSFVRCLLLNRDMDLGSBTLPELLRQQRPSDITCITTYMPVMIARIANIVVRGSKFVEYDDISCN.VQVLQEYT
MDV      NLRLKLAPIMMCKYGTE.....XRSMGDMLRRSAPEDINDSLTLCLILLSRIRRVMHRTSGSKYSYMIDPR..GCMIDYV

HSV-1    PGACMAGLIEILDTHRQECSSRVCBL.TASHIVAPPYVHGKYFYCNSLF
HSV-2    PGACMAGLIEILDTIRQECSSRVCEL.TASHTIAPLYVHGKYFYCNSLP
EHV-1    PGACLAGTLEAIDAHKRRCKADTCSL.VEAYTLVPVYLHGKYFYCIQIF
EHV-4    PGTCLAGTLEAIDLHGRRCKPSTCSL.VESYTLVPVYLHGKYFYCNQIF
BHV-1    PQTCVAGLIDALDTHKQACDSMTCKL.VANFTLVPVYMHGKYFYCNEIP
PRV      PGACLCGIMDALDSHKTGCDAPTCRL.TCSYTLVPVYMHGKYFYCNHLF
VZV      PGSCLAGVLEALITHQRECGRVECTLSTWAGHLSDARPYGKYFXCSTFNC
MDV      PQECMTNILRYVDAHTRRCSDPACNL.YISCTLMPIYIHQRYFYCNTLFGM
```

Betaherpesviruses

```
HHV-6
HHV-7
MCMV
HCMV    MELHSRGRHDAPSLSSLSERERRARRARRPCLDYEPVPRKFRRERSPTSPSTRNGAAASEHHLABDTVGAASHHIRPCVP

HHV-6                                                                                                 HY
HHV-7                                                                                                 MY
MCMV                                                      MLRTGVKRRLGPFAGYDEDUAATGGVSRRSKYSQQQSQHY
HCMV    ARRPRYSKDDDTEGDPDHYPPPLPPSSRHALGGTGGHIIMGTAGPRGGHRASSSPKRRVAASASVPLNPHYGKSYDNDDG

HHV-6   PRGVKRSHHDYHRQTAFRTIKRSTHRQTSKFISHPAKQNFRGKLABLRHC.ESRLDALSLTELEQLKTIIEEKQQEKRAQN
HHV-7   PRGVKKNVLGRQRYGLXTTKRTLVHKPANKYVSRFTKQFHRRIIPIKQLDESKLDALSLRELEQLKLIIEEKQSEKRAQT
MCMV    YYGHNOSSYRDSGASHPNWKRHAHLMPPPLSSPSSPPPQYDKNIAALTHLWKLDCLGPDDLPCLKAMIRIRPAPAQGRR
HCMV    EPHHHGGDSTHLRRRVFSCFTTPGSSHPSSAHNHHGSSAGPQQQQMLALIDDELDAMPEDELQQLSRLIEKKKPARLQRG

HHV-6   NAITFLPNLPTVPPADTNPSLKS..............................LGLRPYNGDARDPKQRIRDRPPQT..HER
HHV-7   HALTFPANLPTAPFGSSYTAEA................................LGLRKYSGEARDPAHRIRDRSPRN..HPK
MCMV    PEPSSAPSILSSLVSSHNSNNNTTLSLGGCGGGDYHRQTSPDIRDYTTGSLGLCMPPMDLPDPIKLLENRYTDNDRHAP
HCMV    AASSGTSPSSTSPVYDLQRYTAES..........................LRLAPYPADLKVPTAPPQDHQPRG....R

HHV-6   ICLLTNDILBTDLLLRYRQCLDSLTREENQQLMGDRIFSLTNSPCLAPTVAIVERACSYFKSHDLHNLPVNPQDLPMYTI
HHV-7   IYLEKBELMTTDLLLAYXNCLMSLWREQHQQILGDRVFSLTNSPSLAFSLAIIEEACIYYKYHFVHNLPIDPQDLPHVTI
MCMV    AVVTHDELINTNYLLLFRKHFDALPPEELRVLVQDRTPAINNAPSLDVVAAMADENLTYVKFIRVBNLPVNPKDLYMSTL
HCMV    ILLSHDELMHTDYLLHIRQQFDWLEEPLLRKLVVEKIPAVYNAPNLHTLLAIIDRTLSYMKYEMLBQLPVNPHDPYLETV

HHV-6   TVMKFEPFNKLNMAKLTCVFNDMGHGDIEYRKLRQLCGKPVLDREMPNSELEVQQQT........PDSFRBPIQQAMSIV
HHV-7   TIMKFEVFNKLNMAKLCCVFNDMGHGDIEYRIFRQLCGKPVYDRDMPNTEYFVQQQT........PGSFQYFAQQALSFI
MCMV    GLIKYATFNKLNLGELGCLLDBPGGGGSDREYHILRQIANKPRSPCRKGDSSAAAAASFDVLRRPPI.SFKHPLQQALALI
HCMV    GCMRQLLFNKLNNLDLGCILDHQDGWGDHCSTLKRLVKKPGQMSAWLRDDVCDLQERP........PETFSQDMHRAMAYV

HHV-6   VTFARILRQIREQIIQTKK.PQPIRDFDTGRVAPRYRCOLMSRLIGKQPENHKCDDVSCQNRIPRIMAPWKPSLFPCTYP
HHV-7   VTFARILRQIKRRILQTRQ.PQPIRDFDQDRVSEQTQCGMISRLVGDQFPNHRQCDDIGCQTRIQRMMSPWKPSLYPCTYL
MCMV    ASFARIVGVIRRRSLRHSG.PPFIRDFDDTGATDSYRCGMISELIPDYLRGHRCQNBICRVKLEKLLQPYTSTLFPCAYN
HCMV    CSFSZVAVSLRRRALQVTGTPQFPDQFDTNNAMGTYRCGAVSDLILGALQCHECQNENCELRIQRALAPYRFMIAYCPFD

HHV-6   AKDAPKFKLFPNPPERYRNLSFTCPKVDTEPSCSYSTNHDLPQTSHRSHKNHGTPKVKSKVCVEKPDTSILTTTKTTTEI
HHV-7   PKRFVBPGLEPNMPEEYNSPNVACSTTPBCSFASQQSKQTVQLNLQTKKQANCKKLLTADKTNNRGQKTNELRENRLEKDW
MCMV    NTRKHPNGTYRREGRQKRRAPDATPNIPRLAYRRSATTSPEVBPAFPBRHTSSSPRVDSRGGGGDRRGDSSSTSSNHHRH
HCMV    EQSLLDLTIVFAGTTTTEASNHATAGGQQRGGDQIHPTDPQYAMMESRTDPATLTAYDKKDREGSHRHPSPMIAAAPPAQP

HHV-6   LIEESKETDNKIPNPRELNFNQAKQERIVIININENVNSKHESPSSSVEMDLCLDVE.ADTCETNLN.ACSEDSE
HHV-7   KSEVDSIDPZTNTTILQRDPTRFVPIENDTSMKSAKIKENNGEENSDNEMELDLDYEDVETCPTDINDTDSDDSD
MCMV    HTRRARTRSTHDSESSGSRRRSSATDGRRSRACSRHGEAQGEHRHSSKS9PSTV3STTVHGQNGARGDEAPSRKSQQSQ
HCMV    PSQPQQHYSEGELEEDEDSDDAASSQDLVRATDRHGOTVVYKTTAVPPSPPAPLAGVRSHRGELNLMTPSPSHGGSPSQVP

MCMV    QQPETTSKESSKTAAMPPPDSDPCSPSPASRERRPSKSPSSSPRPHDPPSGSPADAEKELATAGDEDEGVRSPGECSVATR
HCMV    HXQPIIPVQSANGNHSTTATQQQQPPPPPPPPVPQEDDSVVMRCQTPDYEDMLCYSDDMDD

MCMV    RGSSADESSDESSSSSDSSSSSDEEESDVEDCRELDLQSKRLEEALBERCERDFPADDPEFAEPIRSDDLHCSLDMESDI

MCMV    EDEPLDPETESVWTAGVTPLAAPPSIRILDHEPGDAEEEEESDTDPYDPTDQPLUKRIHLREATPTDDVIMSCDLSYSEMDSD
```

Gammaherpesviruses

```
HHV-8   MVQAMIDMDIM.KGIIB/DSVSSSEVDESRDDFTOAPTLBDEQLSEPAEPPADERIRGTQSAQGIPPPLGRIPKKSQ
HVS     MAQAMVTNCQM.EDIIE/GISSDDDFDSSDSSSDEEBSDTSPQIMKSDVTMASPPSTPEPSFDVSASTSNLKRERQR
BHV-4   MAQAMLTMDCM.REIIB/DLSSDIDSPSGGESIDMESPLEEGEIESDTNSSKPPPPQDLSKPPMMRIPAKRVASPDN
AHV-1   MAQQAIVTMSALRRTMB/VSDSGDVSIDISAEDSNDSFHLEESVDDCMDDCKPHNRPNPISMKPAAERVPMVPIRER
MHV-68  MAQQMLEAGAL.DQMME/GLPSDFDFDTSDEEGELSDSPPVEEPTGFVRDVVVEPDPLFDDPPPTPSPDVKPPSPKA
EBV     MVPSQRLSRTSSISSNEDPA/PSHTLELEAVSDTNTDCDLDPMHEGSEEHSTDGEISSSEEEDEDPTPAHAIPARPSSVVI

HHV-8   GRSQLRESBIQFCSPLSRDRSPSPVNRYCKKIKFGTAGQHTRPPPEKRPRRRPRDRLQYGRTTRGGQCRAAPKRATRRPQV
HVS     SPITWEHQSPLSRVYRSPSPMRFGKRPRISSNSTSRSCKTSWADRVREAAAQRRPSRPFRKPYSRPRTGPLRNGPPRAPP
BHV-4   ERMEYRSPLNRTYPPPPFTERYGKRRRLTAGRPNWSGRVNPDKGRYRRRGLSDNKTIRHTQASIKDBVAVSLRKMKIPTGH
AHV-1   SKTPVQHTSPLNRLYPNVVLGKQHGYKQRPABSARSRRPOPYSARKDSAAKPQSTPSNQNPLTIELLKNVDPAIASRITSM
MHV-68  RKRALSPEIVHNSPLLRDTTKYSPAPKPSYSYHPRRSPQRENAHQKQKRGPDSRRPNRHWNQKSQKQYWSPKPLLDYSKIP
EBV     TPTSASPVIPRKKWDLQDERVTLHRSPLCRDEDEKEETGNSSYTRGHIKRRRGEVHGCTDESYCKRRHLPFGARAPRAPRA

HHV-8   NCQRQDDDVRQGVSDAVKKLRLPASMIIDCESPAPDCSIIPRHHGACPIUSIPAPPSHVP..................EVP
HVS     LLKLFDISILPKSGEPKLPLPVPSLPCQEA..................................................CKT
BHV-4   IERAGEKPPDETLLSSGGPGRYSVPLPRAPEFKL.............................................SRY
AHV-1   RIPRSMLRTPSGQPFAHWNLMPSAEDSSKPINVNPVNMEV......................................CEH
MHV-68  PAEYKNAKLLVPTTGKLRP...........................................................EFY
EBV     PRVPRAPRSPRAPRSNRATRGPRSESRGAGRSTRKQARQERSQRPLPYKPNPDMSLVKPVSKITFVTLPSPLASLTLEPI

HHV-8   TDRDITALIRAGGZDDELIN.KKISAKKIDHLHPQMLSPVTSRHNQAYWVSCRRETAAAGSLCTLGAFVEEQMTWAQTVV
HVS     NDKYVLAMAQRAMHDVPISS.KQLTANLLPVKPKPLLSIVRYTPNYYYWVSMRKSTIASANLCTVAAPTLDBSLCWGGQYL
BHV-4   TDKLVSSLVEKGGENGASIS.RKLSHLKLSSWPSVIHSFLMKSINYHYWVCLRKPTHGSCGLISLMLPLEETCCWPQLCT
AHV-1   VNVVVRRCTEWALISSSRLQD.KSISTKYLAENFYDLRDPAQRSINKSAWINLRREAIAHAGPVNLCAFADEMMMLQLNL
MHV-68  TDRPVDAIIQNAARHCPVSE.KAVSLKNIEESFKLINSFFNSGINKDHWLSTRYFAIFNNGLVVLTHMLDEQLAWAYACL
EBV     QDPFLQSMLAVAAMPEIGAWQEVQPRHELRRSYXTLREPPTKSTNKDTWLDARMQAIQNAGLCTLVAMLEETIFWLQEIT
```

```
HHV-8   RHGGWFDEKDIDIILDTAIFVCNAFVTRFRLL..HLSCVFDKQSELALIKQVAYLVAMGNRLVFACYLLGEVKLNFRGGLL
HVS     KNDFIFSENGKDIILDTSSALLSQLVHKIKMLPFCHCLMQTTPQDHIVKQVCYLIASNNRILDAVRYLQTSVIKSPIVLL
BHV-4   SNDVSINGFSNDIILNSANPLSVQIMFKLRSL..VMPCFAREAHNISLVKQLGYLVSTTNKIQTAASLIRELKLDTKLCLL
AHV-1   NNQGSWKACREDIILTGAPDMCFHALQKVRAF..IKCFLRERHQRALVNALCHIICFEGGIKQAATLCQELFFDPKVGLM
MHV-68  KHGRELP..TDDILMSTSBKLSQQLVIKLIEV..IKCIBKDGIFSRILKGVADAVCLKAQFLRGMITLKRTPCSLPMYTL
EBV     YHGDLPLAPAEDILLACAMSLSKVILTKLKEL..APCFLPNTRDYNFVKQLFYITCATARQNKVVETLSSSYVKQPLCLL

HHV-8   LAFVLTIPGM.QSRRSISARGQELFRTLLEYTRPGDVMGLLNVIVMBHHSLCRNSECAAATRAAMGSAKFNKGLFFYPLS
HVS     LAYAVCLFAA.IICTKNETQLYSHCMRILKEYRPGDVMNILKESLTQHLNKCPSSTCAYTTRAIVGTKANTTGLFFLPTQ
BHV-4   AAFAIVVPTL.LETDKTEHGTYAPFMQYINRYRPGCIMSLYNDVISSBSRECTSRLCIANTRALAGTKDKTKGLFFCPI
AHV-1   VLYFLTPYAPLYSHTIPQCNFGGYFSKCVAQYTPGAUTGLLNSAIEDHYKDCTSQDCTNLITAIVSPETSNKGLLFFPLPM
MHV-68  FVYVLTIPTL..RTRVIRDPLLTQCKDVVLKYQPGDCITLLKAALNCHQCNKDCDKCKYIIDPLLGQTHRTKGVFFVCE
EBV     AAYAAVAPAYINANCRRRHDEVEFLGHYIKNYNPGTLSSLLTEAVETHTRDCRSASCSRLVRAILSPGTGSLQLFFVPGLNQ

HSV     Herpes simplex virus
MCMV    Murine cytomegalovirus
HCMV    Human cytomegalovirus
HVS     Herpesvirus saimiri
MHV     Murine herpesvirus
EBV     Epstein-Barr virus
HHV     Human herpesvirus
EHV     Equine herpesvirus
BHV     Bovine herpesvirus
PRV     Pseudorabies virus
VZV     Varicella-zoster virus
MDV     Marek's disease virus
```

FIGURE 2 ZINC FINGER AMINO ACID CONSERVATION OF IE63

Alphaherpesviruses

```
HSV-1   GVGEXMHFYLPQACMAGLIEILDTHRQECSSRVCEL.TASHIVAPPYVHGKYFYCNSLF    512
HSV-2   GAGETMHFYIPGACMAGLIEILDTHRQBCSSRVCEL.TASHTIAPLYVHGKCFYCNSLF
EHV-1   D.GRVLADYVPGACLAGTLEAIDAHKRRCKADTCSL.VSAYTLVPVYLHGKYFYCNQIF
EHV-4   A.GHALANYVPQTCLAGTLEAIDLHKRRCKESTCSL.VSSYTLVPVYLHGKYFYCNQIF
BHV-1   G.DAPFEEYIPQTCVAGLIDALDTHKQACDSMTCKL.VANFTLVPVYMHGKYFYCNEIP
PRV     S.PVDLEEYVPGACLGGIMDALDSHKTGCDAPTCRL.TCSYTLVPVYMHGKYFYCNHLF
VZV     N.VQVLQEYTPGSCLAGVLEALITHQRECGRVECTLSTWAGHLSDARPYGKYFKCSTFNC
MDV     R..GCMIDYVPCSCMTNILRYVDAHTRRCSDPACNL.YISCTLMPIYIHQRYFYCNTLFGM
                C           H   C   C                                C
```

Betaherpesviruses

```
HHV-6   VTFARILRQIKEQIIQTKK.PQPIRDFDTGRVAERYECOLMSRLIGKQFSNHKCDDVSCQNRIERIMAPWKPSLFFCTY   155
HHV-7   VTFARILRQIKERILQTKQ.PQFIRDFDQDRVSEQYQCGMISRLVGDQFNNHQCDDIGCCQTRIQRMMSPWKPSLYFCTY
MCMV    ASPARIVGVIRRRSLRHSG.PFPIRDFDDTGATDSYRCQMISELIFDYLRGHRCQNEICRVKLKKLLQPYTSTLFPCAY
HCMV    CSFSRVAVSLRRRALQVTGTPQFFDQFDTNNAMGTYRCGAVSDLILGALQCHECQNEMCELRIQRALAPYRFMIAYCPF
                C           H C   C                                C
```

Gammaherpesviruses

```
HHV-8   -LAFVLTIPGM.QSERSISARGQELFRTLLEYYRPGDVWGLLNVIVMEBHSLCRNSECAAATRAAMGSAKFNKGLFFYDLS  455
HVS     LAYAVCLPRA.IICTKNETQLYSHCMRILKGERPGDVMVILHESLTQHLNKCPSSTCAYTTRAIVGTKANTTGLFFLPTQ
BHV-4   AAFAIVVPTL..LETDKTEHGTYAFFMQYINRERPQCIHSLYNDVISSHSRECTSRLCIANTRALAGTKDKTKGLFFCPI
AHV-1   VLYPLTPYAPLYSHTIPQCNFGGYPSKCVAQXTPGAVTGLLNSAIEDHYKDCTSQDCTNLITAIVSPETSHKGLLFFPLPH
MHV-68  FVYVLTIPTL..RTRVIRDPLLTQCKDVVLKYQFGDCITLLKAALNCHQCNKDCDKCKYILDPLLGQTHRTKGVPFVCE
EBV     AAYAAVAPAYINANCRRRHDEVEFLGHYIKNYNPDGTLSSLLTPAVETHTRDCREASCSRLVPAILSPDTGSLGLFFVPGLHQ
                H    C   C
```

```
HSV   Herpes simplex virus
MCMV  Murine cytomegalovirus
HCMV  Human cytomegalovirus
HVS   Herpesvirus saimiri
MHV   Murine herpesvirus
EBV   Epstein-Barr virus
HHV   Human herpesvirus
EHV   Equine herpesvirus
BHV   Bovine herpesvirus
PRV   Pseudorabies virus
VZV   Varicella-zoster virus
MDV   Marek's disease virus
```

HERPES ZINC FINGER MOTIFS

RELATED APPLICATIONS

This application claims priority under 35 U.S.C. § 371 from PCI Application No. PCT/GB01/03114, filed in English on Jul. 11, 2001, which claims the benefit of Great Britain Application Serial No. 0016890.6 filed on Jul. 11, 2000, the disclosures of which are incorporated by reference herein in their entireties.

The present invention relates to a method for detecting an agent for use in the treatment of herpes virus infection and use of known and unknown agents for the manufacture of a medicament for the treatment of herpesvirus infections.

A paradigm for the development of antivirals was based on the identification of agents that selectively eject zinc from retroviral zinc finger proteins. One such protein is the human immunodeficiency HIV-1 nucleocapsid protein NCp7, which is essential for early and late virus replication. NCp7 interacts with the viral RNA at a packaging site (1). This 55 bp amino acid protein contains two zinc fingers, one of which is highly conserved among the retroviruses (reviewed in 2). The NCp7 CCHC zinc finger represents a rare conserved feature, absent in cellular proteins, against the extreme variation of other retrovirus components which suggests that mutation to resistance against reagents that target conserved zinc finger motifs may be difficult to achieve. Potent anti-HIV-1 agents that selectively target the NCp7 protein zinc finger by ejecting zinc have been identified which are non-toxic to cells (3,4).

The following summarised documents describe the use and action of such agents in the treatment of retroviral infections:

Huang et al. 1998 describe agents that target retroviral nucleocapsid protein zinc fingers without seriously affecting cellular zinc finger proteins. Specifically, the agents are 3-nitrosobenzamide (NOBA), disulfide benzamides (DIBAs or 2,2'-dithiobisbenzamides), dithiaheterocyclic molecules such as 1,2-dithiane-4,5-diol, 1,1-dioxide, cis(dithiane), α-carbonyl azoic compounds such as azodicarbonamide (ADA), and others. However, this document only discloses the agents' action on retroviruses and in particular nucleocapsid p7 (NCp7).

Vandervelde et al 1996 describe the anti-HIV-1 properties and clinical/pre-clinical data of 1,1'-azobisformamide (ADA), indicating toxicity studies of the compound in patients.

U.S. Pat. No. 5,516,941 describes c-nitroso compounds which destabilise zinc fingers such as 6-nitroso 1,2-benzopyrone (NOBP), 2-nitrbsobenzamide, 3-nitrosobenzamide (NOBA), 4-nitrosobenzamide, 5-nitroso-1(2H)-isoquinolinone (5-NOQ), 7-nitroso-1(2H) isoquinolin (5-NOQ), 8-nitroso-1(2H)-isoquinolinone (8-NOQ), and related compounds including nicotinamides, pthalhydraziides and 1,3-benzoxazine-2,4 diones for inactivating retroviruses either alone or in combinations thereof. It also provides for methods of detecting compounds that can inactivate retroviruses by testing for the effect of zinc finger destabilising i.e. ejection of zinc measured using NMR.

U.S. Pat. No. 5,463,122 and its divisional application U.S. Pat No. 5,668,178 describe the preparation and use of phenylthiols and dithiobisbenzamides in the treatment of retrovirus infections including HIV treatment.

U.S. Pat. No. 5,585,367 describe the use of azoic compounds (including ADA) in the treatment of retroviral infections. It also details clinical studies on the use of ADA but at no time does the article refer to the drug's use in the treatment of viruses other than retroviruses.

In summary, although some of these documents detail the use and action of specific drugs in the treatment of retroviral infection at no time is it inferred that such drugs can be used in the treatment of non-retrovirus infections such as herpesvirus infections.

Herpesviruses are one of the most important virus families and cause a range of prominent medical or veterinary diseases. Eight different herpesviruses whose natural host is man have been identified so far: herpes simplex virus (HSV) types 1 and 2, varicella-zoster virus (VZV), Epstein-Barr virus, human cytomegalovirus (HCMV) and human herpesvirus (HHV) types 6–8 (reviewed in 5). A large proportion of people world-wide have been exposed to, and may be latently infected with, one or more herpesviruses. Whereas in general an intact immune system keeps these viruses in check, immunocompromised individuals are particularly at risk. HCMV disease in graft recipients, newborns and immunocompromised patients accounts for considerable morbidity. VZV can be a severe and life threatening problem for leukaemic children and patients undergoing chemotherapy or immunosuppressive drug treatment for organ transplants. Herpesviruses have been implicated in the aetiology of different types of cancer with the recently discovered gammaherpesvirus HHV-8 implicated in Kaposi's sarcoma, a major neoplasm of AIDS patients.

At present there are few antiviral agents of broad specificity against the herpesvirus family of viruses (6), and resistance to antiherpesvirus drugs such as acyclovir, against HSV and VZV, and gancyclovir, against HCMV, is an increasing problem (7,8,9), prompting the call for new therapeutic approaches to herpesvirus infections (7).

It is an object of the present invention to obviate and/or mitigate at least some of the above disadvantages.

Broadly speaking, the present invention is based on the present inventors' observation that the spacing and metal co-ordinating residues in the IE63 zinc finger of herpes simplex virus type I are conserved in all related homologues within the alphaherpesvirus sub-family. Similar conservation of spacing of zinc finger motifs but with different arrangements of the conserved motif residues was also discovered by the inventors within the betaherpesvirus and gammaherpesvirus family.

IE63 (also called ICP27) is an essential HSV-1 protein (reviewed in 10). An IE63 homologue exists in all examples of mammalian and avian herpesviruses sequenced so far (around twenty). IE63 is the only HSV-1 immediate early regulatory protein conserved in other herpesvirus indicative of its central role in viral gene regulation. The product of the HSV-1 and HSV-2 UL54 gene, IE63 (ICP27) has counterparts in other herpesviruses namely VZV ORF 4, HCMV UL69, Epstein-Barr virus BMLF1 (SM/MTA), HHV-6 U42, HHV-7 U42, HHV-8 ORF57, equine herpesvirus-1 ORF3, equine herpesvirus-4 ORF3, bovine herpesvirus-1 BICP27, pseudorabies virus UL54, Marek's disease virus UL54, murine cytomegalovirus M69, herpesvirus saimiri ORF57, bovine herpesvirus-4 ORF57, avian herpes virus-1 ORF57 and murine herpesvirus-68 ORF57. HSV-1 IE63 is an essential immediate-early phosphoprotein for the progression of the virus lytic replication cycle from immediate early to early and late stages, its functions affect the transcription of virus genes into RNA and subsequent post-transcriptional processing of this RNA. The action of IE63 is complex, binding other herpesvirus proteins, colocalising with splicing factors and binding RNA with a preference for viral intron-less transcripts (11–13) and inhibiting splicing of both viral and cellular transcripts (14). IE63 causes the nuclear retention of intron-containing transcripts while facilitating the nuclear export of viral intron-less transcripts allowing the virus to take control of host gene expression. The post-transcriptional action of IE63 is even more complex, enhancing 3'RNA processing at late viral poly(A) sites and stabilising 3'ends of mRNA.

IE63 is a zinc finger protein. The yeast genome encodes some 500 zinc finger proteins (reviewed in 11, 12) and estimates are that some 1% of all mammalian genes encode such motifs. The action of zinc fingers include binding to DNA, RNA and DNA-RNA hybrids as well as mediating protein-protein interactions. potentiating self interaction and interactions with other proteins. The IE63 zinc binding region itself (18) is required for self interaction (19, 20) and for interaction with CK2 (19).

The discovery by the present inventors that the spacing and metal co-ordinating residues of the IE63 zinc finger and its homologues are conserved within each of the herpesvirus sub-families (alpha-, beta- and gammaherpesvirus; Example 1)is analogous to the retrovirus HIV-1 protein NCp7, which has been targeted for the development of antivirals that selectively eject zinc (reviewed in 2).

Inspection of the databases reveals that the three conserved zinc finger motifs within the alpha-, beta- and gammaherpesvirus families are divergent to any other identified zinc finger motif present in viral and cellular proteins. Thus, like HIV-1 Ncp7, the IE63 zinc finger represents a rare conserved feature, absent in cellular proteins, against the extreme variation of other virus, in this case herpesvirus, components. This discovery allows the development of new anti-herpes virus agents.

Thus, in a first aspect of the present invention there is provided a method for detecting an agent for use in the treatment of herpes virus infection comprising the steps of:
(a) forming a herpes virus polypeptide/zinc complex;
(b) adding a test agent to said polypeptide/zinc complex; and
(c) detecting any change in the polypeptide/zinc complex.

The method is particularly suited for the detection of agents which may serve as antiherpesvirus agents. The term antiherpesvirus agent is understood to mean an agent which when in contact with a herpesvirus and/or herpesvirus infected cells selectively kills and/or destabilises viruses from this virus family only. Killing or destabilising of herpesviruses may be achieved by, for example, interference of viral nucleic acid synthesis and/or regulation, virus-cell binding, virus uncoating or viral replication. Preferably, the action of the antiherpesvirus agent will not interfere unduly with the infected host cells' machinery.

The term agent is understood to include chemicals, nucleic acid analogues, peptides and/or proteins. For example, these may include C-nitroso and related compounds or disulphide benzamides and azoic compounds such as 2,2'-dithiobisbenzamide (DIBA) and azodicarbonamide (ADA) respectively.

According to the present invention, the term polypeptide refers to herpesvirus HSV-1 and ESV-2 IE63 protein, and counterparts in other herpesviruses namely VZV ORF4, HCMV UL69, Epstein-Barr virus BMLF1 (SM/MTA), HHV-6 U42, HHV-7 U42, HHV-8 ORF57, equine herpesvirus-1 ORF3, equine herpesvirus-4 ORF3, bovine herpesvirus-1 BICP27, pseudorabies virus UL54, Marek's disease virus UL54, murine cytomegalovirus M69, herpesvirus saimiri ORF57, bovine herpesvirus-4 ORF57, avian herpes virus-1 ORF57 and murine herpesvirus-68 ORF57 as shown in FIG. 1, or functional derivatives or functional homologues thereof. In particular, it refers to a polypeptide comprising at least the C-terminal regions of IE63 and homologues as shown in FIG. 2. More particularly, it refers to polypeptides comprising the zinc finger motifs of IE63 homologues of the alpha-, beta- or gammaherpesvirus family as highlighted in bold in FIG. 2.

The term functional derivative thereof according to the present invention refers to any polypeptide containing at least the zinc finger motif of herpesvirus IE63 or its counterparts as shown in FIGS. 1 and 2. The skilled addressee will appreciate that it is possible to manipulate a full-length protein in order to express derivatives of the full-length polypeptide.

Furthermore, the term functional homologue refers to a polypeptide with a sequence similar to those depicted in FIGS. 1 and 2 with a conserved function.

It should be understood that the degree of similarity, over the full-length polypeptide, of functional homologues may vary greatly. That is, a functional homologue is defined by the conservation of amino acid residues in a motif required to characterise a protein family. Thus, there may be a low percentage of similarity of amino acid residues outwith a motif of interest in a full-length polypeptide but as long as said motif is conserved the protein maintains its function and is thus regarded as a functional homologue. In terms of the present invention, it can be seen from FIGS. 1 and 2 that a high percentage of similarity of amino acid residues in herpesvirus IE63 and its homologues is confined to the zinc-finger motif and there is a relative lack of conservation outwith this motif. In particular, functional honologues of IE63, according to the present invention are defined by the precise conservation of spacing and metal co-ordinating amino acid residues in the Zn-finger motif in each of the herpesvirus families. In more detail, Cys-$X_{10}$-His-$X_3$-Cys-$X_4$-Cys-$X_{14}$-His-$X_6$-Cys in the alphaherpesvirus Zn-finger motif, Cys-$X_{12}$-His-$X_1$-Cys-$X_4$-Cys-$X_{17}$-Cys in the betaherpesvirus Zn-finger motif and His-$X_3$-Cys-$X_4$-Cys in the gammaherpesvirus subfamily Zn-finger motif of IE63 functional homologues.

In a further aspect of the present invention there is provided a method for detecting an agent for use in the treatment of herpes virus infection comprising the steps of:
a) forming a herpes virus polypeptide/zinc complex wherein said polypeptide comprises at least the Cys-$X_{10}$-His-$X_3$-Cys-$X_4$-Cys-$X_{14}$-His-$X_6$-Cys alphaherpesvirus subfamily zinc-finger motif, or Cys-$X_{12}$-His-$X_1$-Cys-$X_4$-Cys-$X_{17}$-Cys betaherpesvirus subfamily zinc-finger motif or His-$X_3$-Cys-$X_4$-Cys gammaherpesvirus subfamily zinc finger motif of herpesvirus IE63 functional homologues;
b) adding a test agent to said polypeptide/zinc complex; and
c) detecting any change in the polypeptide/zinc complex.

In order to detect antiherpesvirus agents according to the present invention said polypeptide must first be complexed with zinc. Zinc may be provided in the form of a standard dialysis buffer comprising a known concentration of zinc.

Detection of said antiherpesvirus is based on a change in the properties of said polypeptide/zinc complex when a test agent is added. Said change will be a measure of the test agent's ability to eject zinc and destabilise viral zinc fingers. For example, displacement of zinc from said polypeptide/zinc complex is thus a measure of an agent's potential as an antiherpesvirus agent. It should be understood that the properties of said polypeptide/zinc complex such as concentration and zinc content of (purified) polypeptides may be measured by standard techniques such as standard amino acid analysis and atomic adsorption spectroscopy.

Detection of a change in said polypeptide/zinc complex may be achieved among other methods by using $^{65}Zn^{2+}$ or NMR, which can detect ejection of zinc from said polypeptide/zinc complex by a test agent. For example, for the NCp7 zinc finger domain, loss of NMR signals due to a zinc bound histidine and the appearance of signals representing zinc-free histidine indicates ejection of zinc (21). Preferably, said detection uses spectrofluorimetry as applied to the NCp7 zinc finger (22) with stop flow facilities used to measure on/off rates for zinc binding. Detection of zinc using this method utilises several fluorescent indicators, which exhibit an increase in fluorescence upon binding of zinc. Said fluorescent indicators may, for example, be Newport Green™ or N-(6-methyoxy-8-quinolyl)-p-toluenesulphonamide (25). Thus, for example, said fluorescent indicators may be used to examine for zinc binding, strength of zinc binding and the effect of test agents on a polypeptide/zinc complex according to the present invention.

Generally speaking, any agents detected by the method according to the present invention that cause a change in said polypeptide/zinc complex may be used as an antiherpesvirus agent.

In a further aspect, the present invention also relates to use of an IE63 polypeptide, functional derivative or functional homologue thereof or polypeptide comprising a zinc finger motif as defined herein in the disclosed methods and use of a nucleic acid encoding said polypeptide, in the disclosed methods. Said polypeptide and its functional homologues or derivatives thereof are as described earlier. Generally speaking, the skilled man will understand that the nucleic acid counterparts may be used for cloning, using standard techniques, nucleic acid constructs required for expression of said polypeptide or functional homologue thereof. Optionally, said nucleic acid may be used to clone the C-terminus encoding region of IE63 and its homologues, incorporating the conserved zinc finger motif according to the present invention. Furthermore, they may be used to express and purify said polypeptide. A method of purification of said polypeptide comprising a zinc finger motif can utilise the motif itself. For example, the dimerisation properties of a zinc finger motif can be utilised by binding said polypeptide to Glutathione beads, which are then used to purify further polypeptide from herpesvirus-infected cell extracts through self-interaction of the polypeptide. A further means of providing polypeptide is use of automated peptide synthesis.

In a third aspect, the present invention provides agents detected by the method according to the present invention and their use to treat herpesvirus infections. It should be understood that this may include any suitable pharmaceutical composition comprising, as active substance, any said agent and any synthetic functional derivative thereof. Such agents can also be used in conjunction with known antiherpesvirus agents in the treatment of herpes viral infections as well as, if necessary, one or more pharmaceutical adjuvants. This composition may be administered in any form by various means including topical application to the site of viral breakout eg. mouth for HSV-1 lytic cycle.

The discovery by the present inventors that the spacing and metal co-ordinating residues of the IE63 zinc finger and its homologues are conserved within each of the herpesvirus sub-families (alpha-, beta- and gammaherpesvirus; Example 1)is analogous to the retrovirus HIV-1 protein NCp7, which has been targeted for the development of antivirals that selectively eject zinc (reviewed in 2).

Thus, the present invention further provides the use of previously identified antiretroviral agents in the treatment of herpesvirus infection. Particularly, antiretroviral agents whose action is in the ejection of zinc bound to a zinc finger protein, for example, C-nitroso compounds such as 6-nitroso 1,2-benzopyrone (NOBP), 2-nitrosobenzamide, 3-nitrosobenzamide (NOBA), 4-nitrosobenzamide, 5-nitroso-1(2H)-isoquinolinone (5-NOQ), 7-nitroso-1(2H) isoquinolin (5-NOQ), 8-nitroso-1(2H)-isoquinolinone (8-NOQ), and related compounds including nicotinamides, pthalhydrazides and 1,3-benzoxazine-2,4 diones; phenylthiols; dithiaheterocyclic molecules; disulphide benzamides or azoic compounds. Preferred antiretroviral agents for use according to the present invention are the disulphide benzamide 2,2'-dithiobisbenzamide (DIBA) and azoic compound, azodicarbonamide (ADA). Said antiretroviral agents were identified previously as effective in the treatment of retroviruses only due to their action of Zn-ejection from the zinc finger motif of HIV-1 NCp7.

In a further aspect, the present invention provides the use of such previously identified antiretroviral agents for the manufacture of a medicament for the treatment or prophylaxis of herpes virus infections.

In a yet further aspect there is provided a kit for diagnostic in vitro detection of agents for use in the treatment of herpes virus infection, wherein the kit comprises:
a) a herpes virus polypeptide, said polypeptide comprising a sequence selected from the group consisting of (at least) the Cys-$X_{10}$-His-$X_3$-Cys-$X_4$-Cys-$X_{14}$-His-$X_6$-Cys alphaherpesvirus subfamily zinc-finger motif, Cys-$X_{12}$-His-$X_1$-Cys-$X_4$-Cys-$X_{17}$-Cys betaherpesvirus subfamily zinc-finger motif and His-$X_3$-Cys-$X_4$-Cys gammaherpesvirus subfamily zinc finger motif of herpesvirus IE63 functional homologues;
b) a source of zinc, in order that when added to said polypeptide, a polypeptide/zinc complex is formed; and
c) means for enabling determination of any change in said polypeptide/zinc complex in the presence of an agent.

It may be appreciated that the polypeptide and zinc may be provided as a preformed polypeptide/zinc complex.

Determination of agents for use in the treatment of herpes virus infection is based on a change in the properties of said polypeptide/zinc complex when a test agent is added. Such a change may be determined by methods using $^{65}Zn^{2+}$ or NMR, which can detect ejection of zinc from said polypeptide/zinc complex by a test agent as described earlier.

Typically, said polypeptide or polypeptide/zinc complex may be immobilised on a solid substrate which may be, for example, a well of a microtiter plate, cuvette, nitrocellulose or the like.

The present invention will now be further described by way of example only, with reference to the following methods and figures which show:

FIG. 1—comparison of protein sequences of herpesvirus IE63 and homologues. Alignment of amino acid sequences using the "Pileup" programme (Wisconsin Sequence Package, Version 9.0, Genetics computer Group) of IE63 and its homologues from various human and animal herpesviruses including alpha-, beta- and gammaherpesvirus subfamilies are shown.

FIG. 2—alignment of C-terminal region of IE63 and homologues. Three alignments of the C-terminal region of IE63 and its homologues using the GCG "Pileup" programme are shown for alpha-, beta- and gammaherpesvirus subfamilies. The C-terminal region contains a conserved zinc finger motif within each subfamily of herpesvirus. Conserved residues are shown in bold and denoted by the single letter conserved amino acid residue underneath.

FIG. 3—Gel showing Purification of His tagged IE63 SDS PAGE gel showing the fractions containing IE63 obtained by purification on Qiagen Ni-NTA.

Figure 4:
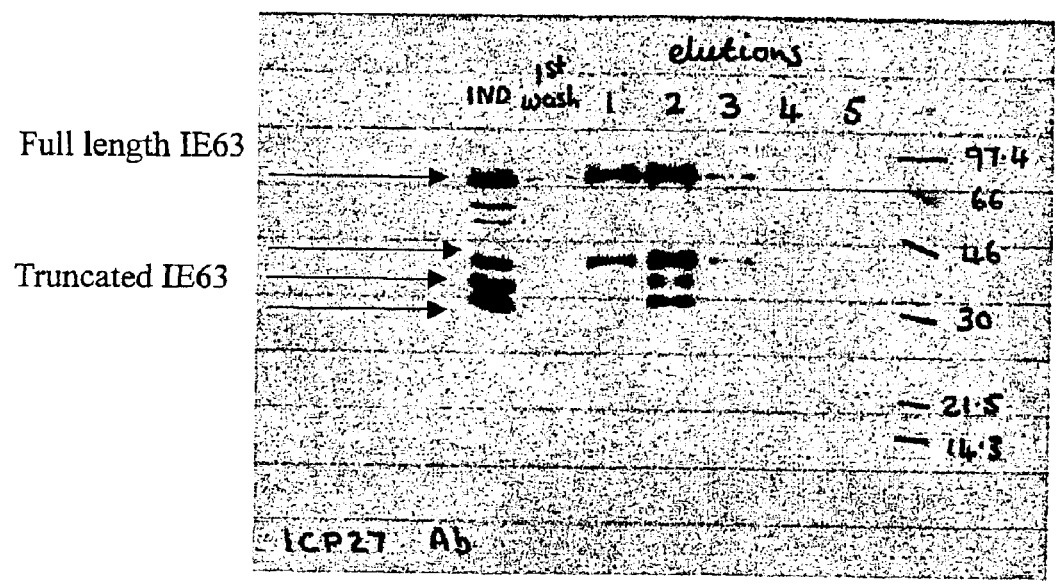

FIG. 4—Western Blot of IE63 Purification Western Blot of fraction obtained from purification of IE63 on Ni-NTA.

Figure 5:
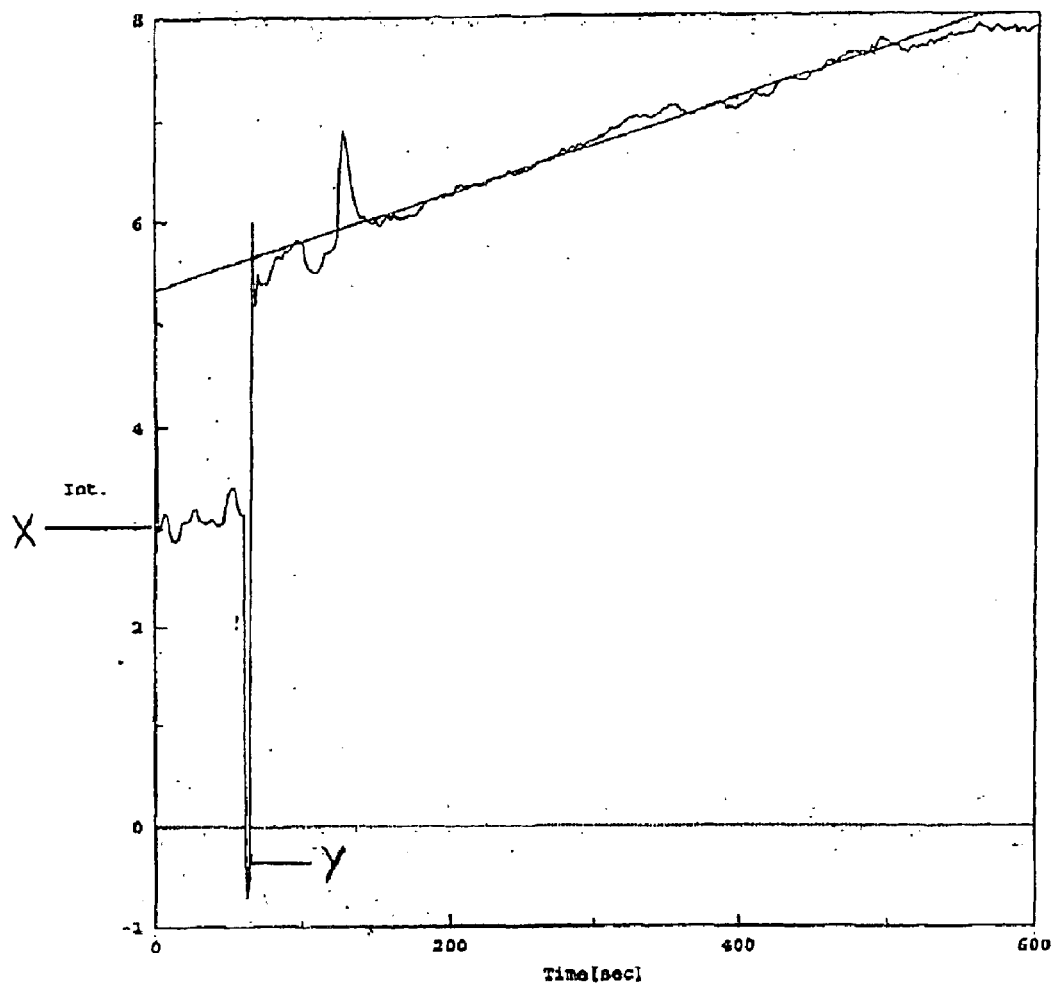

FIG. 5—Zinc election from IE63 monitored by spectrofluorimetry Zinc ejection assay performed on HSV-1 IE63 protein as described in (24). 25 μM TSQ and 0.5 μM IE63 added at time point X. 25 μM DIBA added at time point Y. Excitation wavelength 360 nm and emission wavelength 460 nm, sampling every 2 sec.

METHODS

Cytotoxicity. Both compounds azodicarbonamide (ADA, NSC 674447) and 2,2',-dithiobisbenzamide (DIBA, NSC 654077) were dissolved at the appropriate concentration in 0.1% (v/v) dimethylsulphoxide (DMSO) in Eagle's modified medium. Confluent monolayers ($2 \times 10^6$) of baby hamster kidney BHK21/C13 cells were incubated with various concentrations of either ADA or DIBA (1,10,100 μM) or as a control 0.1% (v/v) DMSO, and cell viability determined every day for 4 days by Trypan Blue exclusion staining (23).

Virus replication. Semi-confluent monolayers of BHK21/C13 cells ($2 \times 10^6$) were pre-incubated with the appropriate drug concentration, 0.1% DMSO (v/v) or mock treated as a control for 24 h and subsequently infected at a multiplicity of infection (moi) of 5 plaque forming units (pfu)/cell with either herpes simplex virus type 1 (HSV-1) strain 17 or HSV-2 strain HG52 and harvested 24 h post-infection (pi). The virus yield was determined by releasing the virus into the supernatant by sonication and titration on BHK21/C13 cells. Results were expressed as pfu/$10^6$ cells and % reduction in yield as compared to the untreated control (23).

Plaque reduction assay. Confluent monolayers ($4 \times 10^6$ cells) of BHK21/C13 cells were preincubated with the appropriate drug concentration, 0.1% DMSO(v/v) or mock treated as a control for 24 h and subsequently infected at a moi of 400 pfu/plate with either HSV-1 or HSV-2 and incubated for 48 h at 37° C. The cells were fixed and stained with Giemsa stain and the number of plaques counted. Tests of each drug concentration were performed in triplicate and the average of the 3 plates calculated. Results were expressed as pfu/plate and % of the number of plaques on the untreated control plates (23).

Expression and Purification of HSV 1 IE63.

Expression of N terminal His Tagged IE63

*E. coli* Novablue cells (Novagen) were transformed with a pET28 vector (Novagen) containing the IE63 gene. Cells were plated on L-Broth Agar containing Tetracycline (12.5 μg/ml) and Kanamycin (25 μg/ml) and incubated overnight at 37° C. The following day a single colony was inoculated into 10 ml of L-Broth containing tetracycline, chloramphenicol and 0.2% maltose and incubated at 37° C. overnight. The next day this 10 ml culture was inoculated into 500 ml of L-Broth (containing tetracycline, chloramphenicol and maltose) and grown at 37° C. until the $OD_{600}$ reached 1.0. $MgSO_4$ was added to a final concentration of 10 mM and the λCE6 phage (Novagen) was added to a final concentration of $2 \times 10^9$ pfu/ml. The cells were grown for a further two hours and then harvested by centrifugation. The pellet of frozen cells was stored frozen at −20° C. until required. Protein expression was analysed by Western blot using the IE63 antibody.

Purification of His Tagged IE63

The pellet of frozen cells was thawed slowly on ice and resuspended in 5 ml of lysis buffer per 500 ml of culture.

Lysis Buffer
2 mM Tris HCl pH 8
100 mM NaCl
0.5% NP-40
20 mM imidazole

Protease inhibitor cocktail tablet (Boehringer). Cells were lysed by French pressing and the insoluble material pelleted by centrifugation at 4° C. and 15000 rpm. The supernatant is removed to a clean tube and 1 ml of Ni-NTA (Qiagen) resin is added per litre of starting culture. This mixture is then incubated with rotation at 4° C. for 2–3 hours. The Ni-NTA resin is pelleted by centrifugation at 3000 rpm for 1 min and the supernatant removed. The resin is then washed with 2 times 50 ml of lysis buffer (described above) followed by one wash with lysis buffer minus NP-40, one wash with lysis buffer plus 1M NaCl and finally one wash with original lysis buffer. The washed beads are then loaded into a 10 ml column (Biorad) and allowed to settle. The protein is eluted from the resin in four to five 1 ml aliquots of elution buffer Elution buffer
20 mM Tris HCl pH 8
100 mM NaCl
300 mM Imidazole The fractions are then analysed by SDS PAGE and Western Blot for the presence of IE63. Fractions containing IE63 are dialysed against 50 mM Tris pH 8 containing 10% glycerol before storing at −20° C.

EXAMPLE 1

Conservation of Zinc Finger Regions in Herpesvirus IE63 and Homologues

Amino acid sequences of herpesvirus IE63 and its various human and animal counterparts were compared using the GCG "Pileup" alignment programme. It was observed that the spacing of the metal co-ordinating cysteine and histidine residues in the IE63 zinc finger (FIG. 1) are precisely conserved in all homologues within the alphaherpesvirus sub-family (Cys-$X_{10}$-His-$X_3$-Cys-$X_4$-Cys-$X_{14}$-His-$X_6$-Cys) and for the other sub-families (FIG. 1) there is a similar conservation of spacing but the arrangements are different (betas; Cys-$X_{12}$-His-$X_1$-Cys-$X_4$-Cys-$X_{17}$-Cys, gammas; His-$X_3$-Cys-$X_4$-Cys). The zinc finger lies at the extreme C-terminus of IE63 and its alphaherpesvirus and betaherpesvirus homologues, and towards the C-terminus in the gammaherpesvirus counterparts. Inspection of the database reveals that these three zinc finger arrangements are different from those present in other identified viral and cellular proteins.

EXAMPLE 2

Determination or cytotoxicity of ADA and DIBA. In view of the distinctive sequence conservation of the IE63 zinc finger two previously known zinc-ejecting anti-HIV-1 compounds, 2,2'-dithiobisbenzamide (DIBA) and azodicarbonamide (ADA) were tested for their effect on herpesvirus. To separate any effect on cell viability from a specific effect on virus replication, the effect of incubating BHK21/C13 cells in various concentrations of ADA, DIBA, and 0.1% (v/v) DMSO as a control, for up to 4 days was determined. Even at the highest concentration used (100 μM) 95% of the cells were viable compared to untreated BHK21/C13 cells (data not shown). Indeed any cytotoxicity observed was due to the DMSO in which the drugs were dissolved, as the cytotoxicity was equally great in those cells incubated with only DMSO (data not shown).

EXAMPLES 3

Antiviral effect of ADA and DIBA. Two experiments were carried out. In the first, the effect of varying concentrations of ADA and DIBA on the replication of HSV-1 was analysed. In the second, the effect on both HSV-1 and HSV-2 was determined. The results are summarised in Tables 1 and 2 respectively.

TABLE 1

| | VIRUS YIELD (pfu/10$^6$ BHK cells) | VIRUS YIELD (pfu/BHK cell) | % UNTREATED CONTROL |
|---|---|---|---|
| HSV-1 | | | |
| 0 | 8 × 10$^8$* | 800 | 100% |
| 0.1% DMSO | 7.2 × 10$^8$ | 720 | 90% |
| 1 μM ADA | 6.1 × 10$^8$ | 610 | 76% |
| 10 μM ADA | 1.5 × 10$^8$ | 150 | 19% |
| 100 μM ADA | 9 × 10$^6$ | 9.0 | 11% |
| 1 μM DIBA | 6.8 × 10$^8$ | 680 | 85% |
| 10 μM DIBA | 1.6 × 10$^8$ | 160 | 20% |
| 100 μM DIBA | 2 × 10$^7$ | 20 | 2.5% |

*each value represents an average of 2 plates

TABLE 2

| | VIRUS YIELD (pfu/10$^6$ BHK cells) | VIRUS YIELD (pfu/BHK cell) | % UNTREATED CONTROL |
|---|---|---|---|
| HSV-1 | | | |
| 0 | 6.1 × 10$^8$* | 610 | 100% |
| 0.1% DMSO | 6 × 10$^8$ | 600 | 98% |
| 1 μM ADA | 9.3 × 10$^7$ | 93 | 15% |
| 10 μM ADA | 8.5 × 10$^6$ | 8.5 | 1.4% |
| 100 μM ADA | 1.2 × 10$^6$ | 1.2 | 0.19% |
| 1 μM DIBA | 1.2 × 10$^8$ | 120 | 20% |
| 10 μM DIBA | 9.6 × 10$^6$ | 9.6 | 1.6% |
| 100 μM DIBA | 1.9 × 10$^6$ | 1.9 | 0.31% |
| HSV-2 | | | |
| 0 | 7 × 10$^7$* | 70 | 100% |
| 0.1% DMSO | 7.2 × 10$^7$ | 72 | 103% |
| 1 μM ADA | 9.4 × 10$^6$ | 9.4 | 13% |
| 10 μM ADA | 8.5 × 10$^5$ | 0.85 | 1.2% |
| 100 μM ADA | 2.3 × 10$^5$ | 0.23 | 0.33% |
| 1 μM DIBA | 1.2 × 10$^7$ | 12 | 17% |
| 10 μM DIBA | 1.4 × 10$^6$ | 1.4 | 2% |
| 100 μM DIBA | 3.1 × 10$^5$ | 0.31 | 0.44% |

*each value represents an average of 2 plates

With both compounds there was a dose dependent reduction in virus yield. In experiment 1, DIBA appeared to have a greater antiviral effect, reducing the virus yield to 2.5% compared to 11% for ADA at 100 μM. However, in the second experiment, where the overall antiviral effect was greater, there was no significant difference between the effect of DIBA and ADA, with virus yield being reduced to less than 1% of the untreated control. Both HSV-1 and HSV-2 replication was equally affected.

EXAMPLE 4

Plaquing Efficiency in the Presence of ADA and DIBA. To determine if the reduction in virus yield seen in the previous experiment was due to a virucidal effect, inhibition of virus entry (adsorption penetration) or intracellular replication, a plaque reduction assay was carried out. Here, the ability of the virus to plaque was measured. An effect on the stability of the virus particle or virus entry would lead to a reduction in the number of plaques compared to the control untreated plates for a given amount of virus. In contrast, an effect on intracellular virus replication would not lead to a significant reduction in plaques. No significant reduction in HSV-1 or HSV-2 plaquing was seen with at most a 10% reduction (i.e. in the presence of the drug 90% of the number of plaques seen with untreated plates still remained) seen at the highest drug concentrations (data not shown). However, there was a reduction in the size of the plaques consistent with an effect on virus replication reducing the yield of progeny virus from each infected cell.

This experiment strongly suggests that the antiviral effect of DIBA seen in the previous experiment is due to an inhibition of intracellular replication.

EXAMPLE 5

Zinc Ejection Assay

Purified HSV-1 IE63 protein was prepared as described earlier for use in the zinc ejection assay. The zinc ejection assay for IE63 was carried out as described in (24) by substituting the IE63 protein for the p7NC protein. All chemicals were used at the same concentrations as described. Results, as measured by spectrofluorimetry are shown in FIG. 5.

It is understood that the above embodiments are merely representative of the present invention and should not be considered to be limiting thereof.

REFERENCES

1. Dannull J, et al (1994). EMBO J., 13, 1525–1533.
2. Rice W G & Turpin J A (1996) Rev. Med. Virol., 6, 187–199.
3. Domagala J M, et al (1997). Bioorganic & Medicinal Chem., 5, 569–579.
4. Huang M, et al (1998) J Med. Chem., 41, 1371–1381.
5. Davison A J & Clemaents J B. (1997). In; Topley and Wilson's Principles of Bacteriology, Virology and Imnunology (9th Edition), eds. B W J Mahy & L H Collier. Edward Arnold, London, pp 309–323.
6. Keating M R (1999). Mayo Clin. Proc., 74, 1266–1283
7. Cassady K A & Whitley R J (1997). J. Antimicrob. Chemother., 39, 119–128.
8. Emery V C (1998) Antivir. Ther., 3, 239–242.
9. Field A K (1999). Antivir. Chem. Chemother., 10, 219–232
10. Phelan A & Clements J B. (1998). Semin. Virol., 8, 309–318.
11. Panagiotidis C A, et al. (1997). J. Virol., 64, 3471–3485.
12. Spengler M et al. (1998). Abstract, 23rd International Herpesvirus Workshop, York, UK.
13. Sandri-Goldin R M (1998). Genes and Dev., 12, 868–878.
14. Hardy W R & Sandri-Goldin R M. (1994). J. Virol., 68, 7790–7799.
16. Choo Y & Klug A (1997). Curr. Opin. Struct. Biol., 7, 117–125.
17. Mackay J P & Crossley M (1998). TIBS, 23, 1–4.
18. Vaughan P J, et al (1992). Virology, 189, 377–384.
19. Wadd S, et al. (1999). J. Biol. Chem., 274, 28991–28998.
20. Zhi Y, et al (1999). Virology, 257, 341–351.
21. Rice W G et al (1993). Nature, 361, 473–475.
22. Rice W G et al (1995). Science, 270, 1194–1197.
23. Dargan, D. J. (1998). In "Herpes Simplex Virus Protocols" Ed. S. M. Brown and A. R. MacLean, Humana Press.
24. Rice et al (1996) Journal of. Medicinal. Chemistry 39 3606–3616. (Evaluation of selected chemotypes in coupled cellular and molecular target based screens identifies novel HIV-1 zinc finger inhibitors).
25. Frederickson, C. J. et al (1987). J. Neurosci. Meth., 20, 91–97.

What is claimed is:

1. A method for detecting an agent for use in the treatment of herpes virus infection comprising the steps of:
   (a) forming a herpes virus polypeptide|zinc complex;
   (b) adding a test agent to said polypeptide/zinc complex; and
   (c) detecting any change in the polypeptide/zinc complex, wherein the herpes virus polypeptide comprises at least one zinc finger motif, and wherein detection of said agent is based on a change in the properties of said polypeptide/zinc complex.

2. A method for detecting an agent for use in the treatment of herpes virus infection according to claim 1 wherein the agent is selected from the group consisting of a chemical, nucleic acid analogue, peptide and protein.

3. A method for detecting an agent for use in the treatment of herpes virus infection according to claim 1 wherein the agent is a C-nitroso and related compound and is selected from the group consisting of 6-nitroso 1,2-benzopyrone (NOBP), 2-nitrosobenzamide, 3-nitrosobenzamide (NOBA), 4-nitrosobenzamide, 5-nitroso-1(2H)-isoquinolinone (5-NOQ), 7-nitroso-1(2H) isoquinolin (5-NOQ), 8-nitroso-1(2H)-isoquinolinone (8-NOQ), and related compounds including nicotinamides, pthalhydrazides and 1,3-benzoxazine-2,4 diones; phenyithiols; dithiaheterocyclic molecules; disulphide benzamides and azoic compounds.

4. A method for detecting an agent for use in the treatment of herpes virus infection according to claim 1 wherein the agent is 2,2'-dithiobisbenzamide (DIBA).

5. A method for detecting an agent for use in the treatment of herpes virus infection according to claim 1 wherein the agent is azodicarbonamide (ADA).

6. A method for detecting an agent for use in the treatment of herpes virus infection according to claim 1 wherein the polypeptide is selected from the group consisting of herpes virus HSV-1 and HSV-2 IE63 protein.

7. A method for detecting an agent for use in the treatment of herpes virus infection according to claim 1 wherein the polypeptide is selected from the group consisting of VZV ORF4, HCMV UL69, Epstein-Barr virus BMLF1 (SM/MTA), HHV-6 U42, HHV-7 U42, HHV-8 ORF57, equine herpes virus-1 ORF3, equine herpes virus-4 ORF3, bovine herpes virus-1 BICP27, pseudorabies virus UL54, Marek's disease virus UL54, murine cytomegalovirus M69, herpes virus saimiri ORF57, bovine herpes virus 4 ORF57, avian herpes virus-1 ORF57 and murine herpes virus-68 ORF57.

8. A method for detecting an agent for use in the treatment of herpes virus infection according to claim 6 wherein the polypeptide comprises at least the C-terminal regions of IE63.

9. A method for detecting an agent for use in the treatment of herpes virus infection according to claim 1 wherein the polypeptide comprises zinc finger motifs selected from the group consisting of Cys-$X_{10}$-His-$X_3$-Cys-$X_4$-Cys-$X_{14}$-His-$X_6$-Cys alphaherpesvirus subfamily zinc-finger motif, Cys-$X_{12}$-His-$X_1$-Cys-$X_4$-Cys-$X_{17}$-Cys betaherpesvirus subfamily zinc-finger motif and His-$X_3$-Cys-$X_4$-Cys gammaherpesvirus subfamily zinc finger motif.

10. A method for detecting an agent for use in the treatment of herpes virus infection according to claim 1 wherein said zinc is provided in the form of a standard dialysis buffer comprising a known concentration of zinc.

11. A method for detecting an agent for use in the treatment of herpes virus infection according to claim 1 wherein said change in the properties of said polypeptide/zinc complex is measured by standard amino acid analysis and atomic absorption spectroscopy.

12. A method for detecting an agent for use in the treatment of herpes virus infection according to claim 1 wherein detection of said agent is a measure of the test agent's ability to eject zinc and/or destabilize viral zinc fingers.

13. A method for detecting an agent for use in the treatment of herpes virus infection according to claim 1 wherein detection of said change in the properties of said polypeptide/zinc complex is achieved by using a selection from the group consisting of $^{65}Zn^{2+}$ and NMR.

14. A method for detecting an agent for use in the treatment of herpes virus infection according to claim 1 wherein detection of said change in the properties of said polypeptide/zinc complex is achieved by using spectrofluorimetry with stop flow facilities.

15. A method for detecting an agent for use in the treatment of herpes virus infection according to claim 1 wherein detection of said change in the properties of said polypeptide/zinc complex is achieved by using spectrofluorimetry with stop flow facilities and wherein said spectrofluorimetry utilizes several fluorescent indicators, which exhibit an increase in fluorescence upon binding of zinc.

16. A method for detecting an agent for use in the treatment of herpes virus infection according to claim 15 wherein said fluorescent indicators include Newport Green™ or N-(6-methyoxy-8-quinolyl)-p-toluenesulphonamide.

17. A method for detecting an agent for use in the treatment of herpes virus infection according to claim 15 wherein said fluorescent indicators are used to examine zinc binding, strength of zinc binding and the effect of said test agents on said polypeptide/zinc complex.

* * * * *

SEQUENCE LISTING

<160> NUMBER OF SEQ ID NOS: 18

<210> SEQ ID NO 1
<211> LENGTH: 512
<212> TYPE: PRT
<213> ORGANISM: herpes simplex virus type 1

<400> SEQUENCE: 1

```
Met Ala Thr Asp Ile Asp Met Leu Ile Asp Leu Gly Leu Asp Leu Ser
1               5                   10                  15

Asp Ser Asp Leu Asp Glu Asp Pro Pro Glu Pro Ala Glu Ser Arg Arg
            20                  25                  30

Asp Asp Leu Glu Ser Asp Ser Ser Gly Glu Cys Ser Ser Ser Asp Glu
        35                  40                  45

Asp Met Glu Asp Pro His Gly Glu Asp Gly Pro Glu Pro Ile Leu Asp
    50                  55                  60

Ala Ala Arg Pro Ala Val Arg Pro Ser Arg Pro Glu Asp Pro Gly Val
65                  70                  75                  80

Pro Ser Thr Gln Thr Pro Arg Pro Thr Glu Arg Gln Gly Pro Asn Asp
                85                  90                  95

Pro Gln Pro Ala Pro His Ser Val Trp Ser Arg Leu Gly Ala Arg Arg
            100                 105                 110

Pro Ser Cys Ser Pro Glu Gln His Gly Gly Lys Val Ala Arg Leu Gln
        115                 120                 125

Pro Pro Pro Thr Lys Ala Gln Pro Ala Arg Gly Gly Arg Arg Gly Arg
    130                 135                 140

Arg Arg Gly Arg Gly Arg Gly Gly Pro Gly Ala Ala Asp Gly Leu Ser
145                 150                 155                 160

Asp Pro Arg Arg Arg Ala Pro Arg Thr Asn Arg Asn Pro Gly Gly Pro
                165                 170                 175

Arg Pro Gly Ala Gly Trp Thr Asp Gly Pro Gly Ala Pro His Gly Glu
            180                 185                 190

Ala Trp Arg Gly Ser Glu Gln Pro Asp Pro Pro Gly Gly Gln Arg Thr
        195                 200                 205

Arg Gly Val Arg Gln Ala Pro Pro Leu Met Thr Leu Ala Ile Ala
    210                 215                 220

Pro Pro Pro Ala Asp Pro Arg Ala Pro Ala Pro Glu Arg Lys Ala Pro
225                 230                 235                 240

Ala Ala Asp Thr Ile Asp Ala Thr Thr Arg Leu Val Leu Arg Ser Ile
                245                 250                 255

Ser Glu Arg Ala Ala Val Asp Arg Ile Ser Glu Ser Phe Gly Arg Ser
            260                 265                 270

Ala Gln Val Met His Asp Pro Phe Gly Gly Gln Pro Phe Pro Ala Ala
        275                 280                 285

Asn Ser Pro Trp Ala Pro Val Leu Ala Gly Gln Gly Gly Pro Phe Asp
    290                 295                 300

Ala Glu Thr Arg Arg Val Ser Trp Glu Thr Leu Val Ala His Gly Pro
305                 310                 315                 320

Ser Leu Tyr Arg Thr Phe Ala Gly Asn Pro Arg Ala Ala Ser Thr Ala
                325                 330                 335

Lys Ala Met Arg Asp Cys Val Leu Arg Gln Glu Asn Phe Ile Glu Ala
            340                 345                 350

Leu Ala Ser Ala Asp Glu Thr Leu Ala Trp Cys Lys Met Cys Ile His
```

```
                355                 360                 365
His Asn Leu Pro Leu Arg Pro Gln Asp Pro Ile Ile Gly Thr Thr Ala
    370                 375                 380

Ala Val Leu Asp Asn Leu Ala Thr Arg Leu Arg Pro Phe Leu Gln Cys
385                 390                 395                 400

Tyr Leu Lys Ala Arg Gly Leu Cys Gly Leu Asp Glu Leu Cys Ser Arg
                405                 410                 415

Arg Arg Leu Ala Asp Ile Lys Asp Ile Ala Ser Phe Val Phe Val Ile
                420                 425                 430

Leu Ala Arg Leu Ala Asn Arg Val Glu Arg Gly Val Ala Glu Ile Asp
                435                 440                 445

Tyr Ala Thr Leu Gly Val Gly Val Gly Glu Lys Met His Phe Tyr Leu
    450                 455                 460

Pro Gly Ala Cys Met Ala Gly Leu Ile Glu Ile Leu Asp Thr His Arg
465                 470                 475                 480

Gln Glu Cys Ser Ser Arg Val Cys Glu Leu Thr Ala Ser His Ile Val
                485                 490                 495

Ala Pro Pro Tyr Val His Gly Lys Tyr Phe Tyr Cys Asn Ser Leu Phe
                500                 505                 510

<210> SEQ ID NO 2
<211> LENGTH: 500
<212> TYPE: PRT
<213> ORGANISM: herpes simplex virus type 2

<400> SEQUENCE: 2

Met Ala Thr Asp Ile Asp Met Leu Ile Asp Leu Gly Leu Asp Leu Ser
1               5                   10                  15

Asp Ser Glu Leu Glu Glu Asp Ala Leu Glu Arg Asp Glu Glu Gly Arg
                20                  25                  30

Arg Asp Asp Pro Glu Ser Asp Ser Ser Gly Glu Cys Ser Ser Ser Asp
            35                  40                  45

Glu Asp Met Glu Asp Pro Cys Gly Asp Gly Ala Glu Ala Ile Asp
    50                  55                  60

Ala Ala Ile Pro Lys Gly Pro Pro Ala Arg Pro Glu Asp Ala Gly Thr
65                  70                  75                  80

Pro Glu Ala Ser Thr Pro Arg Pro Ala Ala Arg Gly Ala Asp Asp
                85                  90                  95

Pro Pro Pro Ala Thr Thr Gly Val Trp Ser Arg Leu Gly Thr Arg Arg
            100                 105                 110

Ser Ala Ser Pro Arg Glu Pro His Gly Gly Lys Val Ala Arg Ile Gln
        115                 120                 125

Pro Pro Ser Thr Lys Ala Pro His Pro Arg Gly Gly Arg Arg Gly Arg
    130                 135                 140

Arg Arg Gly Arg Gly Arg Tyr Gly Pro Gly Gly Ala Asp Ser Thr Pro
145                 150                 155                 160

Lys Pro Arg Arg Arg Val Ser Arg Asn Ala His Asn Gln Gly Gly Arg
                165                 170                 175

His Pro Ala Ser Ala Arg Thr Asp Gly Pro Gly Ala Thr His Gly Glu
            180                 185                 190

Ala Arg Arg Gly Gly Glu Gln Leu Asp Val Ser Gly Gly Pro Arg Pro
        195                 200                 205

Arg Gly Thr Arg Gln Ala Pro Pro Leu Met Ala Leu Ser Leu Thr
    210                 215                 220
```

```
Pro Pro His Ala Asp Gly Arg Ala Pro Val Pro Glu Arg Lys Ala Pro
225                 230                 235                 240

Ser Ala Asp Thr Ile Asp Pro Ala Val Arg Ala Val Leu Arg Ser Ile
                245                 250                 255

Ser Glu Arg Ala Ala Val Glu Arg Ile Ser Glu Ser Phe Gly Arg Ser
            260                 265                 270

Ala Leu Val Met Gln Asp Pro Phe Gly Gly Met Pro Phe Pro Ala Ala
            275                 280                 285

Asn Ser Pro Trp Ala Pro Val Leu Ala Thr Gln Ala Gly Gly Phe Asp
    290                 295                 300

Ala Glu Thr Arg Arg Val Ser Trp Glu Thr Leu Val Ala His Gly Pro
305                 310                 315                 320

Ser Leu Tyr Arg Thr Phe Ala Ala Asn Pro Arg Ala Ala Ser Thr Ala
                325                 330                 335

Lys Ala Met Arg Asp Cys Val Leu Arg Gln Glu Asn Leu Ile Glu Ala
                340                 345                 350

Leu Ala Ser Ala Asp Glu Thr Leu Ala Trp Cys Lys Met Cys Ile His
            355                 360                 365

His Asn Leu Pro Leu Arg Pro Gln Asp Pro Ile Ile Gly Thr Ala Ala
    370                 375                 380

Ala Val Leu Glu Asn Leu Ala Thr Arg Leu Arg Pro Phe Leu Gln Cys
385                 390                 395                 400

Tyr Leu Lys Ala Arg Gly Leu Cys Gly Leu Asp Asp Leu Cys Ser Arg
                405                 410                 415

Arg Arg Leu Ser Asp Ile Lys Asp Ile Ala Ser Phe Val Leu Val Ile
            420                 425                 430

Leu Ala Arg Leu Ala Asn Arg Val Glu Arg Gly Val Ser Glu Ile Asp
            435                 440                 445

Tyr Thr Thr Val Gly Val Gly Ala Gly Glu Thr Met His Phe Tyr Ile
    450                 455                 460

Pro Gly Ala Cys Met Ala Gly Leu Ile Glu Ile Leu Asp Thr His Arg
465                 470                 475                 480

Gln Glu Cys Ser Ser Arg Val Cys Glu Leu Thr Ala Ser His Thr Ile
                485                 490                 495

Ala Pro Leu Tyr
            500

<210> SEQ ID NO 3
<211> LENGTH: 470
<212> TYPE: PRT
<213> ORGANISM: Equine herpesvirus 1

<400> SEQUENCE: 3

Met Ala Leu Ser Ser Val Ser Ser Cys Glu Pro Met Glu Asp Glu Met
1               5                   10                  15

Ser Ile Met Gly Ser Asp Thr Glu Asp Asn Phe Thr Gly Gly Asp Thr
                20                  25                  30

Cys Ala Glu Ala Thr Arg Gly Leu Val Asn Lys Ser Ala Phe Val Pro
            35                  40                  45

Thr Gln Thr Val Gly Thr Val Ser Ala Leu Arg Asn Val Val Gly Asp
    50                  55                  60

Pro Pro Lys Ser Val Val Ser Phe Ser Ala Ser Pro Gln Arg Ala
65                  70                  75                  80

Gln Pro Ser Asn Pro Lys Ser Glu Arg Pro Ala Phe Gly His Gly Arg
                85                  90                  95
```

```
Arg Asn Arg Arg Arg Pro Phe Arg Arg Asn Asn Trp Lys Gln Gln Gln
            100                 105                 110

Arg Gly Trp Glu Lys Pro Glu Pro Glu Asn Val Pro Ala Arg Gln Ser
        115                 120                 125

Ala Gly Ser Trp Pro Lys Arg Ser Ser Leu Pro Val His Met Arg Leu
130             135                 140

Gly Gln Arg Gly Gly Asp Ser Ser Ala Asp Ser Gly His Gly Gly
145             150                 155                 160

Ala Gly Pro Ser Asp Arg Trp Arg Phe Lys Thr Arg Thr Gln Ser Val
                165                 170                 175

Ala Arg Val His Arg Asn Arg Arg Gly Asn Ala Asn His Gly Ser
            180                 185                 190

Asn Thr Pro Gly Arg Ser Ala Gly Asp Arg Leu Asn Ala Ala Ala
            195                 200                 205

Ser Ser Ile Ala Asp Val Cys Arg Arg Val Thr Ser Arg Ile Gly
210                 215                 220

Glu Met Phe His Gly Ala Arg Glu Thr Leu Thr Thr Pro Val Lys Asn
225             230                 235                 240

Gly Gly Phe Arg Ala Glu Asn Ser Ser Pro Trp Ala Pro Val Leu Gly
                245                 250                 255

Phe Gly Ser Asp Gln Phe Asn Pro Glu Ala Arg Arg Ile Thr Trp Asp
                260                 265                 270

Thr Leu Val Glu His Gly Val Asn Leu Tyr Lys Leu Phe Glu Val Arg
            275                 280                 285

Ser His Ala Ala Glu Ala Ala Arg Ser Leu Arg Asp Ala Val Met Arg
290                 295                 300

Gly Glu Asn Leu Leu Glu Ala Leu Ala Ser Ala Asp Glu Thr Leu Ser
305                 310                 315                 320

Trp Cys Lys Met Ile Val Thr Lys Asn Leu Pro Met Arg Thr Arg Asp
            325                 330                 335

Pro Ile Ile Ser Ser Ser Val Ala Leu Leu Asp Asn Leu Arg Leu Lys
            340                 345                 350

Leu Glu Pro Phe Met Arg Cys Tyr Leu Ser Ser Ser Gly Ser Pro Thr
            355                 360                 365

Leu Ala Glu Leu Cys Asp His Gln Arg Leu Ser Asp Val Ala Cys Val
370                 375                 380

Pro Thr Phe Met Phe Val Met Leu Ala Arg Ile Ala Arg Ala Val Gly
385                 390                 395                 400

Ser Gly Ala Glu Thr Val Ser Arg Asp Ala Leu Gly Pro Asp Gly Arg
            405                 410                 415

Val Leu Ala Asp Tyr Val Pro Gly Ala Cys Leu Ala Gly Thr Leu Glu
            420                 425                 430

Ala Ile Asp Ala His Lys Arg Arg Cys Lys Ala Asp Thr Cys Ser Leu
            435                 440                 445

Val Ser Ala Tyr Thr Leu Val Pro Val Tyr Leu His Gly Lys Tyr Phe
450                 455                 460

Tyr Cys Asn Gln Ile Phe
465             470

<210> SEQ ID NO 4
<211> LENGTH: 467
<212> TYPE: PRT
<213> ORGANISM: Equine herpesvirus 4
```

-continued

```
<400> SEQUENCE: 4

Met Ala Leu Ser Ser Val Ser Ser Cys Glu Pro Met Asp Asp Glu Met
 1               5                  10                  15

Ser Ile Met Gly Ser Asp Thr Asp Thr Leu Gly Gly Ser Cys Val
             20                  25                  30

Glu Ala Ala Gln Ser Ala Val Val Asn Lys Arg Ala Phe Glu Met Ser
             35                  40                  45

Glu Ser Thr Gly Thr Met Ser Thr Ile Arg Asn Val Val Ser Glu Val
     50                  55                  60

Pro Lys Ser Leu Val Ser Phe Ala Ala Ser Pro Lys Asn Pro Lys
 65              70                  75                  80

Pro Gln Asn Thr Thr Ser Glu Arg Ser Ala Phe Pro His Gly Arg Lys
                 85                  90                  95

Asn Arg Arg Arg Pro Phe Arg Arg Asn Asn Trp Lys Gln Arg Ala Trp
                100                 105                 110

Glu Lys Gln Ser Gln Glu Ala Ala Pro Ala Asn Gln Gly Ser Arg Asn
            115                 120                 125

Trp Pro Lys Arg Ser Ser Met Pro Val His Met Arg Leu Gly His Arg
130                 135                 140

Ser Gly Asp Phe Gln Ser Ala Asp Ala Gly His Cys Thr Ala Gly Pro
145                 150                 155                 160

Ser Gly Gly Trp Arg Phe Lys Thr Arg Thr His Ser Ala Ser Arg Val
                165                 170                 175

Tyr His Asn Arg Gln Arg Gly Asn Thr Asn Lys Ser Gly Asn Ala Ser
            180                 185                 190

Ser Arg Ser Ser Gly Asp Arg Leu Asn Ala Ala Ala Asn Ala Ile
        195                 200                 205

Ala Asp Val Ser Lys Arg Val Thr Ser Ser Arg Ile Ser Asp Met Phe
    210                 215                 220

His Gly Ala Arg Glu Thr Leu Thr Ser Pro Val Lys Asn Gly Gly Phe
225                 230                 235                 240

Arg Ala Glu His Ser Ser Pro Trp Ser Pro Val Leu Asn Phe Gly Leu
                245                 250                 255

Glu Gln Phe Asn Pro Glu Gly Arg Arg Ile Thr Trp Asp Thr Leu Val
            260                 265                 270

Thr His Gly Glu Asn Leu Tyr Lys Leu Phe Glu Val Arg Ser His Ala
        275                 280                 285

Ala Glu Ala Ala Arg Ser Leu Arg Asp Leu Val Met Arg Gly Glu Asn
    290                 295                 300

Leu Leu Glu Ala Leu Ala Ser Ala Asp Glu Thr Ile Ser Trp Cys Lys
305                 310                 315                 320

Met Ile Ile Thr Lys Asn Leu Pro Met Arg Thr Arg Asp Pro Ile Ile
                325                 330                 335

His Ser Ser Ile Ala Leu Leu Glu Asn Leu Arg Leu Lys Leu Glu Pro
            340                 345                 350

Phe Met Arg Cys Tyr Leu Ser Ser Ser Gly Ser Pro Thr Leu Ala Glu
        355                 360                 365

Leu Cys Asp His Gln Arg Leu Ser Asp Val Ala Cys Val Pro Thr Phe
    370                 375                 380

Met Phe Val Thr Leu Ala Arg Ile Ala Arg Ala Val Gly Ser Gly Ala
385                 390                 395                 400

Glu Ala Val Ser Pro Asp Ala Leu Gly Pro Ala Gly His Ala Leu Ala
                405                 410                 415
```

-continued

```
Asn Tyr Val Pro Gly Thr Cys Leu Ala Gly Thr Leu Glu Ala Ile Asp
            420                 425                 430

Leu His Lys Arg Arg Cys Lys Glu Ser Thr Cys Ser Leu Val Ser Ser
            435                 440                 445

Tyr Thr Leu Val Pro Val Tyr Leu His Gly Lys Tyr Phe Tyr Cys Asn
            450                 455                 460

Gln Ile Phe
465

<210> SEQ ID NO 5
<211> LENGTH: 400
<212> TYPE: PRT
<213> ORGANISM: Bovine herpesvirus 1

<400> SEQUENCE: 5

Met Ala Asp Pro Glu Ile Ala Thr Leu Ser Thr Ala Ser Glu Ser Asp
1               5                   10                  15

Asp Leu Ser Leu Phe Gly Ser Asp Arg Glu Glu Asp Asp Glu Ala Pro
            20                  25                  30

Ser Leu Ala Pro Ala Leu Arg Ser Val Val Gly Gln Val Arg Lys Arg
            35                  40                  45

Lys Leu Glu Gly Ala Glu Asp Glu Pro Met Pro Ala Glu Pro Pro Gly
        50                  55                  60

Glu Gly Ala Ala Ser Gly Asp Gly Gly Pro Ala Glu Ala Pro Pro Ala
65                  70                  75                  80

Arg Arg Ala Arg Val Arg Pro Arg Arg Pro Arg Arg Pro Arg Arg
            85                  90                  95

Arg Gln Pro Ala Gly Glu Gln Arg Ser Arg Gly Pro Ala Ala Lys Arg
            100                 105                 110

Glu Ala Ala Leu Ala Thr Ser Ser His Gly Gly Gly Gly Ala Ala Ala
            115                 120                 125

Arg Ser Ile Gly Ser Ser Leu Arg Leu Ala Arg Ser Leu Ala Glu Ala
        130                 135                 140

Ala Gln Arg Ala Thr Ala Glu Arg Val Thr Ala Val Phe Ala Gly Ala
145                 150                 155                 160

Arg Leu Asp Leu Met Arg Pro Val Gln Asn Gly Gly Phe Arg Ala Ala
            165                 170                 175

Gly Val Ser Pro Trp Ala Ala Val Leu Asp Phe Gly Ala Glu Gln Phe
            180                 185                 190

Val Pro Glu Gly Arg Arg Val Thr Trp Glu Thr Leu Met Phe His Gly
            195                 200                 205

Arg Asp Leu Tyr Arg Met Phe Glu Val Arg Pro His Ala Ala Gln Ala
        210                 215                 220

Ala Arg Ala Leu Arg Asp Leu Val Leu Arg Ser Ala Asn Leu Val Asp
225                 230                 235                 240

Ala Leu Ala Ser Ala Asp Glu Cys Leu Thr Trp Cys Lys Phe Ile Ala
            245                 250                 255

Thr Lys Asn Leu Arg Leu Arg Thr Lys Asp Pro Ile Val Ala Thr Ala
            260                 265                 270

Gly Ala Val Leu Glu Asn Leu Arg Leu Lys Leu Ala Pro Phe Leu Arg
            275                 280                 285

Cys Tyr Leu Arg Gly Arg Gly Leu Pro Ser Leu Glu Glu Leu Cys Ala
            290                 295                 300

Ala Arg Arg Leu Ser Leu Ala Thr Cys Pro Ala Ser Tyr Met Phe Val
```

```
            305                 310                 315                 320
Met Leu Ala Arg Leu Ser Arg Ala Val Arg Ser Gly Ala Glu Cys Val
                325                 330                 335

Pro Leu Glu Val Thr Val Gly Asp Ala Pro Phe Glu Glu Tyr Ile
            340                 345                 350

Pro Gly Thr Cys Val Ala Gly Leu Ile Asp Ala Leu Asp Thr His Lys
                355                 360                 365

Gln Ala Cys Asp Ser Met Thr Cys Lys Leu Val Ala Asn Phe Thr Leu
            370                 375                 380

Val Pro Val Tyr Met His Gly Lys Tyr Phe Tyr Cys Asn Glu Ile Phe
385                 390                 395                 400

<210> SEQ ID NO 6
<211> LENGTH: 361
<212> TYPE: PRT
<213> ORGANISM: Pseudorabies virus

<400> SEQUENCE: 6

Met Glu Asp Ser Gly Asn Ser Ser Gly Ser Glu Ala Ser Arg Ser Gly
1               5                   10                  15

Ser Glu Glu Arg Arg Pro Val Arg Glu Arg Leu Gly Ser Arg Pro Pro
                20                  25                  30

Glu Arg Arg Pro Val Arg Ala Arg Leu Gly Ala Ile Arg Arg Arg Arg
            35                  40                  45

Gly Gly Arg Gly Gly Arg Ala Ala Arg Gln Ala Leu Arg Gln Arg Arg
        50                  55                  60

Arg Gln Gln Gln Gln Gln Arg Gln Gln His Gln Arg Arg
65                  70                  75                  80

Gln Glu Ala Asp Arg Pro Asp Gly Gly Pro Asp Ala Pro Pro Asp Arg
                85                  90                  95

Leu Ser Glu Ser Ala Arg Ala Ala Val Ser Ala Thr His Ala Arg Val
            100                 105                 110

Gly Ala Thr Arg Val Asn Glu Leu Phe Ala Ser Ala Arg His Asp Leu
        115                 120                 125

Ser Arg Pro Val Phe Asn Asp Gly Phe Arg Ala Ala Gly Ser Ser Pro
    130                 135                 140

Trp Ala Val Leu Glu Phe Gly Ala Glu Gln Phe Thr Pro Asp Gly
145                 150                 155                 160

Arg Arg Val Thr Trp Glu Thr Leu Met Phe His Gly Ala Asp Leu His
                165                 170                 175

Arg Leu Phe Glu Val Arg Pro His Ala Thr Glu Ala Ala Arg Val Leu
            180                 185                 190

Arg Glu Met Val Leu Leu Asn Glu Gly Leu Thr Glu Ser Leu Ala Ser
        195                 200                 205

Ala Asp Glu Thr Leu Thr Trp Val Lys Leu Ile Leu Thr Lys Gly Leu
    210                 215                 220

Thr Leu Arg Thr Leu Asp Pro Ile Val Ala Thr Ala Gly Ala Val Leu
225                 230                 235                 240

Gln Asn Leu Arg Leu Lys Leu Gly Pro Phe Leu Arg Cys Tyr Leu Arg
                245                 250                 255

Asp Thr Pro Val Asp Glu Leu Val Arg Arg Arg Leu Arg Asp Val
            260                 265                 270

Arg Cys Ile Val Thr Tyr Thr Leu Val Met Leu Ala Arg Ile Ala Arg
        275                 280                 285
```

```
Val Val Glu Arg Gly Ser Ser Cys Val Leu Pro Glu Asp Leu Gly Asp
    290                 295                 300

Ser Pro Val Pro Leu Glu Glu Tyr Val Pro Gly Ala Cys Leu Gly Gly
305                 310                 315                 320

Ile Met Asp Ala Leu Asp Ser His Lys Thr Gly Cys Asp Ala Pro Thr
                325                 330                 335

Cys Arg Leu Thr Cys Ser Tyr Thr Leu Val Pro Val Tyr Met His Gly
            340                 345                 350

Lys Tyr Phe Tyr Cys Asn His Leu Phe
            355                 360

<210> SEQ ID NO 7
<211> LENGTH: 452
<212> TYPE: PRT
<213> ORGANISM: Varicella-zoster virus

<400> SEQUENCE: 7

Met Ala Ser Ala Ser Ile Pro Thr Asp Pro Asp Val Ser Thr Ile Cys
1               5                   10                  15

Glu Asp Phe Met Asn Leu Leu Pro Asp Glu Pro Ser Asp Asp Phe Ala
                20                  25                  30

Leu Glu Val Thr Asp Trp Ala Asn Asp Glu Ala Ile Gly Ser Thr Pro
            35                  40                  45

Gly Glu Asp Ser Thr Thr Ser Arg Thr Val Tyr Val Glu Arg Thr Ala
50                  55                  60

Asp Thr Ala Tyr Asn Pro Arg Tyr Ser Lys Arg Arg His Gly Arg Arg
65                  70                  75                  80

Glu Ser Tyr His His Asn Arg Pro Lys Thr Leu Val Val Val Leu Pro
                85                  90                  95

Asp Ser Asn His His Gly Gly Arg Asp Val Glu Thr Gly Tyr Ala Arg
                100                 105                 110

Ile Glu Arg Gly His Arg Arg Ser Ser Arg Ser Tyr Asn Thr Gln Ser
            115                 120                 125

Ser Arg Lys His Arg Asp Arg Ser Leu Ser Asn Arg Arg Arg Arg Pro
130                 135                 140

Thr Thr Pro Pro Ala Met Thr Thr Gly Glu Arg Asn Asp Gln Thr His
145                 150                 155                 160

Asp Glu Ser Tyr Arg Leu Arg Phe Ser Lys Arg Asp Ala Arg Arg Glu
                165                 170                 175

Arg Ile Arg Lys Glu Tyr Asp Ile Pro Val Asp Arg Ile Thr Gly Arg
            180                 185                 190

Ala Ile Glu Val Val Ser Thr Ala Gly Ala Ser Val Thr Ile Asp Ser
            195                 200                 205

Val Arg His Leu Asp Glu Thr Ile Glu Lys Leu Val Val Arg Tyr Ala
210                 215                 220

Thr Ile Gln Glu Gly Asp Ser Trp Ala Ser Gly Cys Phe Pro Gly
225                 230                 235                 240

Ile Lys Gln Asn Thr Ser Trp Pro Glu Leu Met Leu Tyr Gly His Glu
                245                 250                 255

Leu Tyr Arg Thr Phe Glu Ser Tyr Lys Met Asp Ser Arg Ile Ala Arg
            260                 265                 270

Ala Leu Arg Glu Arg Val Ile Arg Gly Glu Ser Leu Ile Glu Ala Leu
            275                 280                 285

Glu Ser Ala Asp Glu Leu Leu Thr Trp Ile Lys Met Leu Ala Ala Lys
290                 295                 300
```

```
Asn Leu Pro Ile Tyr Thr Asn Pro Ile Val Ala Thr Ser Lys Ser
305                 310                 315                 320

Leu Leu Glu Asn Leu Lys Leu Lys Leu Gly Pro Phe Val Arg Cys Leu
            325                 330                 335

Leu Leu Asn Arg Asp Asn Asp Leu Gly Ser Arg Thr Leu Pro Glu Leu
            340                 345                 350

Leu Arg Gln Gln Arg Phe Ser Asp Ile Thr Cys Ile Thr Thr Tyr Met
        355                 360                 365

Phe Val Met Ile Ala Arg Ile Ala Asn Ile Val Val Arg Gly Ser Lys
    370                 375                 380

Phe Val Glu Tyr Asp Asp Ile Ser Cys Asn Val Gln Val Leu Gln Glu
385                 390                 395                 400

Tyr Thr Pro Gly Ser Cys Leu Ala Gly Val Leu Glu Ala Leu Ile Thr
                405                 410                 415

His Gln Arg Glu Cys Gly Arg Val Glu Cys Thr Leu Ser Thr Trp Ala
            420                 425                 430

Gly His Leu Ser Asp Ala Arg Pro Tyr Gly Lys Tyr Phe Lys Cys Ser
        435                 440                 445

Thr Phe Asn Cys
    450

<210> SEQ ID NO 8
<211> LENGTH: 473
<212> TYPE: PRT
<213> ORGANISM: Marek's disease virus

<400> SEQUENCE: 8

Met Ser Val Asp Ala Phe Ser Arg Glu Ser Asp Asp Met Met Ser Leu
1               5                   10                  15

Leu Asp Tyr Asp Phe Ile Glu Gly Ser Ser Ser Asp Glu Asn Ala Glu
            20                  25                  30

Val Thr Glu Met Glu Thr Ser Ala Lys Thr Ala Asn Asn Lys Asn Glu
        35                  40                  45

Val Leu Phe Ala Pro Pro Cys Thr Gln Glu Leu Leu Thr Glu Arg Pro
    50                  55                  60

Ser Pro Asp Ser Lys Asn Ser Gln Gly Asp Asp Ser Asn Ser Ile
65                  70                  75                  80

Tyr Gly Asn Val Ile Arg Asp Ala Gln His Ser Ala Ser Arg Tyr Ala
                85                  90                  95

Thr Arg Cys Leu Asp Asn Ala Ile Pro Arg Lys Arg Leu Arg Leu Ala
            100                 105                 110

Asn Leu Thr Val Asp Ser Ala Cys Ile Ser Gln Thr Lys Arg Pro His
        115                 120                 125

Gly Thr Gly Asn Arg Lys Gln Tyr His Arg Arg Asn Phe Pro Met Ser
    130                 135                 140

Pro Thr Ser Gln Glu Lys Ile His Leu Arg Leu His Asn Arg Leu Gly
145                 150                 155                 160

Ser Arg Ser Glu Lys Gln Gln Arg Ser Leu Asn Tyr Asp Arg Arg Leu
                165                 170                 175

Gln Glu Gly His His Arg Arg Phe Tyr Ser Glu Arg Arg Ile Tyr
            180                 185                 190

Asp Gln Asn His Ser His His Arg Thr His Asp Ile Arg Val Pro Leu
        195                 200                 205

Glu Lys Tyr Arg Val Ser Arg Gln His Asp Leu Pro Val His Glu Glu
```

```
                    210                 215                 220
Leu Asn Glu Ile Leu Gln Arg Glu Lys His Arg Leu Ala Ser Ile Ser
225                 230                 235                 240

Asn Glu Cys Asp Phe Arg Val Ser Ser Lys Asn Arg Trp Ala Ala Val
            245                 250                 255

Leu Thr Phe Ser Ser Asn Ala Glu Ser Thr Leu Cys Gly Pro Gln Ile
        260                 265                 270

Thr Trp Glu Tyr Leu Leu His Ala Gly Pro Glu Leu Arg Asn Thr Phe
            275                 280                 285

Glu Ile Arg Pro Arg Ile Ser Leu Gln Ala Ser Ala Arg Glu Ala
    290                 295                 300

Val Leu Arg Gly Glu Ser Phe Ile Ala Ala Leu Gly Ser Ala Glu Glu
305                 310                 315                 320

Thr Leu Ser Trp Leu Lys Leu His Ala Val Leu Lys Leu Arg Leu Val
                325                 330                 335

Asn His Asp Pro Ile Phe Lys Thr Ala Gly Ala Val Leu Asp Asn Leu
            340                 345                 350

Arg Leu Lys Leu Ala Pro Ile Met Met Cys Lys Tyr Gly Thr Glu Lys
        355                 360                 365

Arg Ser Met Gly Asp Met Leu Arg Arg Ser Ala Pro Glu Asp Ile Asn
370                 375                 380

Asp Ser Leu Thr Leu Cys Leu Ile Leu Leu Ser Arg Ile Arg Arg Val
385                 390                 395                 400

Met His Arg Thr Ser Gly Ser Lys Tyr Ser Tyr Met Ile Asp Pro Arg
                405                 410                 415

Gly Cys Met Ile Asp Tyr Val Pro Gly Glu Cys Met Thr Asn Ile Leu
            420                 425                 430

Arg Tyr Val Asp Ala His Thr Arg Arg Cys Ser Asp Pro Ala Cys Asn
        435                 440                 445

Leu Tyr Ile Ser Cys Thr Leu Met Pro Ile Tyr Ile His Gly Arg Tyr
    450                 455                 460

Phe Tyr Cys Asn Thr Leu Phe Gly Met
465                 470

<210> SEQ ID NO 9
<211> LENGTH: 515
<212> TYPE: PRT
<213> ORGANISM: Human herpesvirus 6

<400> SEQUENCE: 9

Met Tyr Pro Arg Gly Val Lys Arg Ser His His Asp Tyr His Arg Gln
1               5                   10                  15

Thr Ala Phe Arg Thr Ile Lys Arg Ser Thr His Arg Gln Thr Ser Lys
            20                  25                  30

Phe Ile Ser His Phe Ala Lys Asn Phe Arg Gly Lys Leu Ala Pro Leu
        35                  40                  45

Lys Gln Leu Asp Glu Ser Arg Leu Asp Ala Leu Ser Leu Thr Glu Leu
    50                  55                  60

Glu Gln Leu Lys Thr Ile Ile Glu Glu Lys Gln Gln Glu Lys Arg Ala
65                  70                  75                  80

Gln Asn Asn Ala Ile Thr Phe Leu Pro Asn Leu Pro Thr Val Pro Phe
                85                  90                  95

Ala Asp Thr Asn Phe Ser Leu Lys Ser Leu Gly Leu Arg Pro Tyr Asn
            100                 105                 110
```

```
Gly Asp Ala Arg Asp Pro Lys Gln Arg Ile Arg Asp Arg Phe Pro Gln
    115                 120                 125

Thr His Glu Arg Ile Cys Leu Leu Thr Asn Asp Ile Leu Glu Thr Asp
    130                 135                 140

Leu Leu Leu Arg Tyr Arg Gln Cys Leu Asp Ser Leu Thr Arg Glu Glu
145                 150                 155                 160

Asn Gln Gln Leu Met Gly Asp Arg Ile Phe Ser Leu Thr Asn Ser Pro
                165                 170                 175

Cys Leu Ala Phe Thr Val Ala Thr Val Glu Glu Ala Cys Ser Tyr Phe
                180                 185                 190

Lys Phe His Asp Leu His Asn Leu Pro Val Asn Pro Gln Asp Leu Phe
            195                 200                 205

Met Tyr Thr Ile Thr Val Met Lys Phe Glu Phe Asn Lys Leu Asn
    210                 215                 220

Met Ala Lys Leu Thr Cys Val Phe Asn Asp Asn Gly His Gly Asp Ile
225                 230                 235                 240

Glu Tyr Arg Lys Leu Arg Gln Leu Cys Gly Lys Pro Val Leu Asp Arg
                245                 250                 255

Glu Met Pro Asn Ser Glu Leu Glu Val Gln Gln Gln Thr Pro Asp Ser
                260                 265                 270

Phe Arg His Pro Ile Gln Gln Ala Met Ser Ile Val Val Thr Phe Ala
            275                 280                 285

Arg Ile Leu Arg Gln Ile Lys Glu Gln Ile Ile Gln Thr Lys Lys Pro
    290                 295                 300

Gln Phe Ile Arg Asp Phe Asp Thr Gly Arg Val Ala Glu Arg Tyr Glu
305                 310                 315                 320

Cys Gly Leu Met Ser Arg Leu Ile Gly Lys Gln Phe Ser Asn His Lys
                325                 330                 335

Cys Asp Asp Val Ser Cys Gln Asn Arg Ile Glu Arg Ile Met Ala Pro
                340                 345                 350

Trp Lys Pro Ser Leu Phe Phe Cys Thr Tyr Phe Ala Lys Asp Ala Pro
            355                 360                 365

Lys Phe Lys Leu Phe Pro Asn Phe Pro Glu Glu Tyr Arg Asn Leu Ser
    370                 375                 380

Phe Thr Cys Pro Lys Val Asp Thr Glu Pro Ser Cys Ser Tyr Ser Thr
385                 390                 395                 400

Asn His Asp Leu Pro Gln Thr Ser His Arg Ser His Lys Asn His Gly
                405                 410                 415

Thr Pro Lys Val Lys Ser Lys Val Cys Val Glu Lys Pro Asp Thr Ser
                420                 425                 430

Ile Leu Thr Thr Thr Lys Thr Thr Thr Glu Ile Leu Ile Glu Glu Ser
            435                 440                 445

Met Glu Thr Asp Asn Lys Ile Pro Asn Pro Arg Glu Leu Asn Phe Asn
    450                 455                 460

Gln Ala Lys Gln Glu Glu Ile Val Ile Ile Asn Ile Asn Glu Asn Val
465                 470                 475                 480

Asn Ser Lys His Glu Ser Glu Ser Ser Val Glu Met Asp Leu Asp Leu
                485                 490                 495

Asp Tyr Glu Ala Asp Thr Cys Glu Thr Asn Leu Asn Ala Cys Ser Ser
                500                 505                 510

Asp Ser Glu
    515
```

<210> SEQ ID NO 10
<211> LENGTH: 516
<212> TYPE: PRT
<213> ORGANISM: Human herpesvirus 7

<400> SEQUENCE: 10

| | | | | | | | | | | | | | | | |
|---|---|---|---|---|---|---|---|---|---|---|---|---|---|---|---|
| Met | Tyr | Pro | Arg | Gly | Val | Lys | Lys | Asn | Val | Leu | Gly | Arg | Gln | Arg | Tyr |
| 1 | | | | 5 | | | | | 10 | | | | | 15 | |
| Gly | Leu | Lys | Thr | Ile | Lys | Arg | Thr | Leu | Val | His | Lys | Pro | Ala | Asn | Lys |
| | | | 20 | | | | | 25 | | | | | 30 | | |
| Tyr | Val | Ser | Arg | Phe | Thr | Lys | Gln | Phe | His | Arg | Arg | Ile | Ile | Pro | Ile |
| | | 35 | | | | | 40 | | | | | 45 | | | |
| Lys | Gln | Leu | Asp | Glu | Ser | Lys | Leu | Asp | Ala | Leu | Ser | Leu | Arg | Glu | Leu |
| | 50 | | | | | 55 | | | | | 60 | | | | |
| Glu | Gln | Leu | Lys | Leu | Ile | Ile | Glu | Glu | Lys | Gln | Glu | Glu | Lys | Arg | Ala |
| 65 | | | | | 70 | | | | | 75 | | | | | 80 |
| Gln | Thr | His | Ala | Leu | Thr | Phe | Phe | Ala | Asn | Leu | Pro | Thr | Ala | Pro | Phe |
| | | | | 85 | | | | | 90 | | | | | 95 | |
| Gly | Ser | Ser | Tyr | Thr | Ala | Glu | Ala | Leu | Gly | Leu | Arg | Lys | Tyr | Ser | Gly |
| | | | 100 | | | | | 105 | | | | | 110 | | |
| Glu | Ala | Arg | Asp | Pro | Ala | His | Arg | Ile | Arg | Asp | Arg | Phe | Pro | Arg | Asn |
| | | 115 | | | | | 120 | | | | | 125 | | | |
| His | Glu | Lys | Ile | Tyr | Leu | Glu | Lys | Glu | Leu | Met | Thr | Thr | Asp | Leu |
| | 130 | | | | | 135 | | | | | 140 | | | | |
| Leu | Leu | Arg | Tyr | Lys | Asn | Cys | Leu | Asn | Ser | Leu | Asn | Arg | Glu | Gln | His |
| 145 | | | | | 150 | | | | | 155 | | | | | 160 |
| Gln | Gln | Ile | Leu | Gly | Asp | Arg | Val | Phe | Ser | Leu | Thr | Asn | Ser | Pro | Ser |
| | | | | 165 | | | | | 170 | | | | | 175 | |
| Leu | Ala | Phe | Ser | Leu | Ala | Ile | Ile | Glu | Glu | Ala | Cys | Ile | Tyr | Tyr | Lys |
| | | | 180 | | | | | 185 | | | | | 190 | | |
| Tyr | His | Phe | Val | His | Asn | Leu | Pro | Ile | Asp | Pro | Gln | Asp | Leu | Phe | Met |
| | | 195 | | | | | 200 | | | | | 205 | | | |
| Tyr | Thr | Ile | Thr | Ile | Met | Lys | Phe | Glu | Tyr | Phe | Asn | Lys | Leu | Asn | Met |
| | 210 | | | | | 215 | | | | | 220 | | | | |
| Ala | Lys | Leu | Cys | Cys | Val | Phe | Asn | Asp | Asn | Gly | His | Gly | Asp | Ile | Glu |
| 225 | | | | | 230 | | | | | 235 | | | | | 240 |
| Tyr | Arg | Ile | Phe | Arg | Gln | Leu | Cys | Gly | Lys | Pro | Val | Tyr | Asp | Arg | Asp |
| | | | | 245 | | | | | 250 | | | | | 255 | |
| Met | Pro | Asn | Thr | Glu | Tyr | Glu | Val | Gln | Gln | Thr | Pro | Gly | Ser | Phe |
| | | | 260 | | | | | 265 | | | | | 270 | | |
| Gln | Tyr | Pro | Ala | Gln | Gln | Ala | Leu | Ser | Phe | Ile | Val | Thr | Phe | Ala | Arg |
| | | 275 | | | | | 280 | | | | | 285 | | | |
| Ile | Leu | Arg | Gln | Ile | Lys | Glu | Arg | Ile | Leu | Gln | Thr | Lys | Gln | Pro | Gln |
| | 290 | | | | | 295 | | | | | 300 | | | | |
| Phe | Ile | Arg | Asp | Phe | Asp | Gln | Asp | Arg | Val | Ser | Glu | Gln | Tyr | Gln | Cys |
| 305 | | | | | 310 | | | | | 315 | | | | | 320 |
| Gly | Met | Ile | Ser | Arg | Leu | Val | Gly | Asp | Gln | Phe | Asn | Asn | His | Gln | Cys |
| | | | | 325 | | | | | 330 | | | | | 335 | |
| Asp | Asp | Ile | Gly | Cys | Gln | Thr | Arg | Ile | Gln | Arg | Met | Met | Ser | Pro | Trp |
| | | | 340 | | | | | 345 | | | | | 350 | | |
| Lys | Pro | Ser | Leu | Tyr | Phe | Cys | Thr | Tyr | Leu | Pro | Lys | Glu | Phe | Val | Glu |
| | | 355 | | | | | 360 | | | | | 365 | | | |
| Phe | Gly | Leu | His | Pro | Asn | Met | Pro | Glu | Glu | Tyr | Asn | Ser | Phe | Asn | Val |
| | 370 | | | | | 375 | | | | | 380 | | | | |

-continued

```
Ala Cys Ser Thr Thr Pro Ser Cys Ser Phe Ala Ser Gln Gln Ser Lys
385                 390                 395                 400

Gln Thr Val Gln Leu Asn Leu Gln Thr Lys Lys Gln Ala Lys Cys Lys
            405                 410                 415

Lys Leu Leu Thr Ala Asp Lys Thr Asn Lys Gly Gln Lys Thr Asn Glu
        420                 425                 430

Leu Arg Glu Asn Arg Leu Lys Lys Asp Trp Ser Lys Glu Val Asp Ser
    435                 440                 445

Ile Asp Phe Glu Thr Asn Thr Thr Leu Gln Glu Asp Glu Thr Arg Phe
450                 455                 460

Val Phe Ile Glu Asn Asp Thr Ser Met Lys Ser Ala Lys Ile Lys Glu
465                 470                 475                 480

Asn Asn Gly Glu Glu Asn Ser Asp Asn Glu Met Glu Leu Asp Leu Asp
            485                 490                 495

Tyr Glu Asp Val Glu Thr Cys Glu Thr Asp Ile Asn Asp Thr Asp Ser
        500                 505                 510

Asp Asp Ser Asp
    515

<210> SEQ ID NO 11
<211> LENGTH: 841
<212> TYPE: PRT
<213> ORGANISM: Murine cytomegalovirus

<400> SEQUENCE: 11

Met Leu Arg Thr Gly Val Lys Arg Arg Leu Gly Pro Phe Ala Gly Tyr
1               5                   10                  15

Asp Glu Asp Asp Ala Ala Thr Gly Gly Val Ser Arg Arg Ser Lys Tyr
            20                  25                  30

Ser Gln Gln Gln Ser Gln His Tyr Tyr Tyr Gly His Asn Gln Ser Ser
        35                  40                  45

Tyr Arg Asp Ser Gly Ala Ser His Pro Asn Trp Lys Arg Asn Ala His
50                  55                  60

Leu Met Pro Pro Pro Leu Ser Ser Pro Ser Ser Pro Pro Gln Tyr
65                  70                  75                  80

Asp Lys Asn Ile Ala Ala Leu Thr His Leu Asn Lys Lys Leu Asp Cys
            85                  90                  95

Leu Gly Pro Asp Asp Leu Glu Cys Leu Lys Ala Met Ile Arg Ile Arg
        100                 105                 110

Glu Ala Arg Ala Gln Gly Arg Arg Pro Glu Pro Ser Ser Ala Pro Ser
    115                 120                 125

Ile Leu Glu Ser Ser Leu Val Ser Ser Asn Ser Asn Asn Thr
130                 135                 140

Thr Leu Ser Leu Gly Gly Gly Gly Gly Asp Tyr His Arg Gln Thr
145                 150                 155                 160

Ser Pro Asp Ile Arg Asp Tyr Thr Thr Gly Ser Leu Gly Leu Cys Met
            165                 170                 175

Phe Pro Met Asp Leu Pro Asp Pro Ile Lys Leu Leu Glu Asn Arg Tyr
        180                 185                 190

Thr Asp Asn Asp Arg His Ala Pro Ala Val Val Thr His Asp Glu Leu
    195                 200                 205

Ile Asn Thr Asn Tyr Leu Leu Leu Phe Arg Lys His Phe Asp Ala Leu
210                 215                 220

Pro Pro Glu Glu Leu Arg Val Leu Val Gln Asp Arg Thr Phe Ala Ile
225                 230                 235                 240
```

-continued

```
Asn Asn Ala Pro Ser Leu Asp Val Val Ala Ala Met Ala Asp Glu Asn
                245                 250                 255
Leu Thr Tyr Val Lys Phe His Arg Val His Asn Leu Pro Val Asn Pro
            260                 265                 270
Lys Asp Leu Tyr Met Ser Thr Leu Gly Leu Ile Lys Tyr Ala Thr Phe
        275                 280                 285
Asn Lys Leu Asn Leu Gly Glu Leu Ser Cys Leu Leu Asp Ser Pro Gly
    290                 295                 300
Gly Gly Gly Ser Asp Arg Glu Tyr His Ile Leu Arg Gln Ile Ala Asn
305                 310                 315                 320
Lys Pro Ala Ser Pro Cys Arg Lys Gly Gly Ser Ser Ala Ala Ala Ala
                325                 330                 335
Ala Ser Phe Asp Val Leu Arg Arg Pro Pro Leu Ser Phe Lys His Pro
            340                 345                 350
Leu Gln Gln Ala Leu Ala Leu Ile Ala Ser Phe Ala Arg Ile Val Gly
        355                 360                 365
Val Ile Arg Arg Arg Ser Leu Arg His Ser Gly Pro Phe Phe Ile Arg
    370                 375                 380
Asp Phe Asp Asp Thr Gly Ala Thr Asp Ser Tyr Arg Cys Gly Met Ile
385                 390                 395                 400
Ser Glu Leu Ile Phe Asp Tyr Leu Pro Gly His Arg Cys Gln Asn Glu
                405                 410                 415
Ile Cys Arg Val Lys Leu Lys Leu Leu Gln Pro Tyr Thr Ser Thr
            420                 425                 430
Leu Phe Phe Cys Ala Tyr Asn Asn Thr Arg Lys His Pro Asn Gly Leu
        435                 440                 445
Pro Ala Arg Arg Ser Pro Glu Arg Arg Ala Pro Asp Ala Thr Pro Asn
    450                 455                 460
Ile Pro Arg Leu Ala Tyr Arg Arg Ser Ala Thr Thr Ser Pro Glu Val
465                 470                 475                 480
Glu Pro Ala Pro Pro Ser Arg Met Thr Ser Ser Ser Pro Arg Val Asp
                485                 490                 495
Ser Arg Gly Gly Gly Gly Asp Arg Arg Gly Asp Ser Ser Thr Ser
            500                 505                 510
Ser Asn His His Arg His His Thr Arg Ala Arg Thr Arg Ser Thr
        515                 520                 525
His Asp Ser Ser Ser Ser Gly Ser Arg Arg Ser Ser Ala Thr Asp
    530                 535                 540
Gly Arg Arg Ser Arg Arg Gly Ser Arg Arg Gly Glu Ala Gln Arg Glu
545                 550                 555                 560
Ser Asn Gly His His Ser Ser Lys Ser Pro Ser Thr Val Ser Ser Thr
                565                 570                 575
Thr Val His Gly Gln Asn Gly Ala Arg Gly Asp Ser Ala Pro Ser Arg
            580                 585                 590
Lys Ser Gln Gln Ser Gln Gln Gln Pro Glu Thr Thr Ser Lys Glu Ser
        595                 600                 605
Ser Lys Thr Ala Ala Met Pro Pro Pro Ser Pro Cys Ser Pro Ser
    610                 615                 620
Pro Ala Ser Arg Glu Arg Arg Pro Ser Lys Ser Ser Ser Ser Pro
625                 630                 635                 640
Arg Pro His Asp Pro Pro Ser Gly Glu Pro Ala Asp Ala Glu Lys Glu
                645                 650                 655
```

-continued

```
Leu Ala Thr Ala Gly Asp Glu Asp Glu Gly Val Arg Ser Pro Gly Glu
            660                 665                 670
Cys Ser Val Ala Thr Arg Arg Gly Ser Ser Ala Asp Glu Ser Ser Asp
            675                 680                 685
Ser Ser Ser Ser Ser Ser Asp Ser Ser Ser Ser Asp Glu Glu Glu
            690                 695                 700
Ser Asp Val Glu Asp Cys Arg Glu Leu Asp Leu Gln Ser Lys Arg Leu
705                 710                 715                 720
Glu Glu Ala Leu Glu Glu Arg Cys Glu Arg Asp Phe Glu Ala Asp Asp
                725                 730                 735
Glu Glu Phe Ala Glu Pro Ile Glu Glu Asp Leu His Cys Ser Leu
            740                 745                 750
Asp Met Glu Glu Asp Ile Glu Asp Glu Pro Leu Asp Pro Glu Thr Glu
            755                 760                 765
Ser Val Trp Thr Ala Ser Val Thr Pro Leu Ala Ala Pro Pro Ser Ile
770                 775                 780
Arg Ile Leu Asp His Glu Pro Gly Asp Ala Glu Glu Glu Glu Ser
785                 790                 795                 800
Asp Thr Asp Phe Tyr Asp Glu Thr Asp Gln Pro Leu Asn Lys Arg Ile
                805                 810                 815
His Leu Arg Ser Ala Thr Pro Thr Asp Asp Val Ile Met Glu Cys Asp
            820                 825                 830
Leu Ser Tyr Ser Glu Met Asp Ser Asp
            835                 840

<210> SEQ ID NO 12
<211> LENGTH: 744
<212> TYPE: PRT
<213> ORGANISM: Human cytomegalovirus

<400> SEQUENCE: 12

Met Glu Leu His Ser Arg Gly Arg His Asp Ala Pro Ser Leu Ser Ser
1               5                   10                  15
Leu Ser Glu Arg Glu Arg Arg Ala Arg Arg Ala Arg Arg Phe Cys Leu
            20                  25                  30
Asp Tyr Glu Pro Val Pro Arg Lys Phe Arg Arg Glu Arg Ser Pro Thr
        35                  40                  45
Ser Pro Ser Thr Arg Asn Gly Ala Ala Ala Ser Glu His His Leu Ala
    50                  55                  60
Glu Asp Thr Val Gly Ala Ala Ser His His Arg Pro Cys Val Pro
65                  70                  75                  80
Ala Arg Arg Pro Arg Tyr Ser Lys Asp Asp Thr Glu Gly Asp Pro
                85                  90                  95
Asp His Tyr Pro Pro Leu Pro Pro Ser Ser Arg His Ala Leu Gly
            100                 105                 110
Gly Thr Gly Gly His Ile Ile Met Gly Thr Ala Gly Phe Arg Gly Gly
            115                 120                 125
His Arg Ala Ser Ser Ser Phe Lys Arg Arg Val Ala Ala Ser Ala Ser
    130                 135                 140
Val Pro Leu Asn Pro His Tyr Gly Lys Ser Tyr Asp Asn Asp Asp Gly
145                 150                 155                 160
Glu Pro His His His Gly Gly Asp Ser Thr His Leu Arg Arg Val
                165                 170                 175
Pro Ser Cys Pro Thr Thr Phe Gly Ser Ser His Pro Ser Ser Ala Asn
            180                 185                 190
```

```
Asn His His Gly Ser Ser Ala Gly Pro Gln Gln Gln Met Leu Ala
        195                 200                 205
Leu Ile Asp Asp Glu Leu Asp Ala Met Asp Glu Asp Glu Leu Gln Gln
        210                 215                 220
Leu Ser Arg Leu Ile Glu Lys Lys Arg Ala Arg Leu Gln Arg Gly
225                 230                 235                 240
Ala Ala Ser Ser Gly Thr Ser Pro Ser Thr Ser Pro Val Tyr Asp
                245                 250                 255
Leu Gln Arg Tyr Thr Ala Glu Ser Leu Arg Leu Ala Pro Tyr Pro Ala
        260                 265                 270
Asp Leu Lys Val Pro Thr Ala Phe Pro Gln Asp His Gln Pro Arg Gly
        275                 280                 285
Arg Ile Leu Leu Ser His Asp Glu Leu Met His Thr Asp Tyr Leu Leu
        290                 295                 300
His Ile Arg Gln Gln Phe Asp Trp Leu Glu Glu Pro Leu Leu Arg Lys
305                 310                 315                 320
Leu Val Val Glu Lys Ile Phe Ala Val Tyr Asn Ala Pro Asn Leu His
                325                 330                 335
Thr Leu Leu Ala Ile Ile Asp Glu Thr Leu Ser Tyr Met Lys Tyr His
                340                 345                 350
His Leu His Gly Leu Pro Val Asn Pro His Asp Pro Tyr Leu Glu Thr
        355                 360                 365
Val Gly Gly Met Arg Gln Leu Leu Phe Asn Lys Leu Asn Asn Leu Asp
        370                 375                 380
Leu Gly Cys Ile Leu Asp His Gln Asp Gly Trp Gly Asp His Cys Ser
385                 390                 395                 400
Thr Leu Lys Arg Leu Val Lys Lys Pro Gly Gln Met Ser Ala Trp Leu
                405                 410                 415
Arg Asp Asp Val Cys Asp Leu Gln Lys Arg Pro Pro Glu Thr Phe Ser
                420                 425                 430
Gln Pro Met His Arg Ala Met Ala Tyr Val Cys Ser Phe Ser Arg Val
        435                 440                 445
Ala Val Ser Leu Arg Arg Arg Ala Leu Gln Val Thr Gly Thr Pro Gln
450                 455                 460
Phe Phe Asp Gln Phe Asp Thr Asn Asn Ala Met Gly Thr Tyr Arg Cys
465                 470                 475                 480
Gly Ala Val Ser Asp Leu Ile Leu Gly Ala Leu Gln Cys His Glu Cys
                485                 490                 495
Gln Asn Glu Met Cys Glu Leu Arg Ile Gln Arg Ala Leu Ala Pro Tyr
                500                 505                 510
Arg Phe Met Ile Ala Tyr Cys Pro Phe Asp Glu Gln Ser Leu Leu Asp
        515                 520                 525
Leu Thr Val Phe Ala Gly Thr Thr Thr Thr Ala Ser Asn His Ala
        530                 535                 540
Thr Ala Gly Gly Gln Gln Arg Gly Gly Asp Gln Ile His Pro Thr Asp
545                 550                 555                 560
Glu Gln Tyr Ala Asn Met Glu Ser Arg Thr Asp Pro Ala Thr Leu Thr
                565                 570                 575
Ala Tyr Asp Lys Lys Asp Arg Glu Gly Ser His Arg His Pro Ser Pro
                580                 585                 590
Met Ile Ala Ala Ala Pro Pro Ala Gln Pro Pro Ser Gln Pro Gln Gln
        595                 600                 605
```

-continued

His Tyr Ser Glu Gly Glu Leu Glu Glu Asp Glu Asp Ser Asp Asp Ala
610                 615                 620

Ser Ser Gln Asp Leu Val Arg Ala Thr Asp Arg His Gly Asp Thr Val
625                 630                 635                 640

Val Tyr Lys Thr Thr Ala Val Pro Pro Ser Pro Pro Ala Pro Leu Ala
            645                 650                 655

Gly Val Arg Ser His Arg Gly Glu Leu Asn Leu Met Thr Pro Ser Pro
            660                 665                 670

Ser His Gly Gly Ser Pro Pro Gln Val Pro His Lys Gln Pro Ile Ile
            675                 680                 685

Pro Val Gln Ser Ala Asn Gly Asn His Ser Thr Thr Ala Thr Gln Gln
        690                 695                 700

Gln Gln Pro Pro Pro Pro Pro Pro Pro Pro Val Pro Gln Glu Asp
705                 710                 715                 720

Asp Ser Val Val Met Arg Cys Gln Thr Pro Asp Tyr Glu Asp Met Leu
                725                 730                 735

Cys Tyr Ser Asp Asp Met Asp Asp
            740

<210> SEQ ID NO 13
<211> LENGTH: 455
<212> TYPE: PRT
<213> ORGANISM: human herpesvirus 8

<400> SEQUENCE: 13

Met Val Gln Ala Met Ile Asp Met Asp Ile Met Lys Gly Ile Leu Glu
1               5                   10                  15

Asp Ser Val Ser Ser Ser Glu Phe Asp Glu Ser Arg Asp Asp Glu Thr
                20                  25                  30

Asp Ala Pro Thr Leu Glu Asp Glu Gln Leu Ser Glu Pro Ala Glu Pro
            35                  40                  45

Pro Ala Asp Glu Arg Ile Arg Gly Thr Gln Ser Ala Gln Gly Ile Pro
        50                  55                  60

Pro Pro Leu Gly Arg Ile Pro Lys Lys Ser Gln Gly Arg Ser Gln Leu
65                  70                  75                  80

Arg Ser Glu Ile Gln Phe Cys Ser Pro Leu Ser Arg Pro Arg Ser Pro
                85                  90                  95

Ser Pro Val Asn Arg Tyr Gly Lys Lys Ile Lys Phe Gly Thr Ala Gly
                100                 105                 110

Gln Asn Thr Arg Pro Pro Glu Lys Arg Pro Arg Arg Pro Arg
            115                 120                 125

Asp Arg Leu Gln Tyr Gly Arg Thr Thr Arg Gly Gly Gln Cys Arg Ala
        130                 135                 140

Ala Pro Lys Arg Ala Thr Arg Pro Gln Val Asn Cys Gln Arg Gln
145                 150                 155                 160

Asp Asp Asp Val Arg Gln Gly Val Ser Asp Ala Val Lys Lys Leu Arg
                165                 170                 175

Leu Pro Ala Ser Met Ile Ile Asp Gly Glu Ser Pro Arg Phe Asp Asp
            180                 185                 190

Ser Ile Ile Pro Arg His His Gly Ala Cys Phe Asn Val Phe Ile Pro
        195                 200                 205

Ala Pro Pro Ser His Val Pro Glu Val Phe Thr Arg Asp Ile Thr
210                 215                 220

Ala Leu Ile Arg Ala Gly Gly Lys Asp Asp Glu Leu Ile Asn Lys Lys
225                 230                 235                 240

```
Ile Ser Ala Lys Lys Ile Asp His Leu His Arg Gln Met Leu Ser Phe
            245                 250                 255

Val Thr Ser Arg His Asn Gln Ala Tyr Trp Val Ser Cys Arg Arg Glu
            260                 265                 270

Thr Ala Ala Gly Gly Leu Gln Thr Leu Gly Ala Phe Val Glu Glu
            275                 280                 285

Gln Met Thr Trp Ala Gln Thr Val Val Arg His Gly Gly Trp Phe Asp
            290                 295                 300

Glu Lys Asp Ile Asp Ile Ile Leu Asp Thr Ala Ile Phe Val Cys Asn
305                 310                 315                 320

Ala Phe Val Thr Arg Phe Arg Leu Leu His Leu Ser Cys Val Phe Asp
            325                 330                 335

Lys Gln Ser Glu Leu Ala Leu Ile Lys Gln Val Ala Tyr Leu Val Ala
            340                 345                 350

Met Gly Asn Arg Leu Val Glu Ala Cys Asn Leu Leu Gly Glu Val Lys
            355                 360                 365

Leu Asn Phe Arg Gly Gly Leu Leu Ala Phe Val Leu Thr Ile Pro
370                 375                 380

Gly Met Gln Ser Arg Arg Ser Ile Ser Ala Arg Gly Gln Glu Leu Phe
385                 390                 395                 400

Arg Thr Leu Leu Glu Tyr Tyr Arg Pro Gly Asp Val Met Gly Leu Leu
            405                 410                 415

Asn Val Ile Val Met Glu His His Ser Leu Cys Arg Asn Ser Glu Cys
            420                 425                 430

Ala Ala Ala Thr Arg Ala Ala Met Gly Ser Ala Lys Phe Asn Lys Gly
            435                 440                 445

Leu Phe Phe Tyr Pro Leu Ser
            450                 455

<210> SEQ ID NO 14
<211> LENGTH: 426
<212> TYPE: PRT
<213> ORGANISM: Herpesvirus saimiri

<400> SEQUENCE: 14

Met Ala Gln Ala Met Val Thr Asn Cys Gln Met Glu Asp Ile Ile Glu
1               5                   10                  15

Gly Ile Ser Ser Asp Asp Phe Asp Ser Ser Asp Ser Ser Asp
            20                  25                  30

Glu Glu Glu Ser Asp Thr Ser Pro Gln Ile Met Lys Ser Asp Val Thr
            35                  40                  45

Met Ala Ser Pro Pro Ser Thr Pro Glu Pro Ser Pro Asp Val Ser Ala
    50                  55                  60

Ser Thr Ser Asn Leu Lys Arg Glu Arg Gln Arg Ser Pro Ile Thr Trp
65                  70                  75                  80

Glu His Gln Ser Pro Leu Ser Arg Val Tyr Arg Ser Pro Ser Pro Met
                85                  90                  95

Arg Phe Gly Lys Arg Pro Arg Ile Ser Ser Asn Ser Thr Ser Arg Ser
            100                 105                 110

Cys Lys Thr Ser Trp Ala Asp Arg Val Arg Glu Ala Ala Ala Gln Arg
            115                 120                 125

Arg Pro Ser Arg Pro Phe Arg Lys Pro Tyr Ser His Pro Arg Asn Gly
            130                 135                 140

Pro Leu Arg Asn Gly Pro Pro Arg Ala Pro Pro Leu Leu Lys Leu Phe
```

-continued

```
                145                 150                 155                 160
Asp Ile Ser Ile Leu Pro Lys Ser Gly Glu Pro Lys Leu Phe Leu Pro
                    165                 170                 175
Val Pro Ser Leu Pro Cys Gln Glu Ala Glu Lys Thr Asn Asp Lys Tyr
                180                 185                 190
Val Leu Ala Met Ala Gln Arg Ala Met His Asp Val Pro Ile Ser Ser
            195                 200                 205
Lys Gln Leu Thr Ala Asn Leu Leu Pro Val Lys Phe Lys Pro Leu Leu
        210                 215                 220
Ser Ile Val Arg Tyr Thr Pro Asn Tyr Tyr Trp Val Ser Met Arg
225                 230                 235                 240
Lys Glu Thr Ile Ala Ser Ala Asn Leu Cys Thr Val Ala Ala Phe Leu
                245                 250                 255
Asp Glu Ser Leu Cys Trp Gly Gln Gln Tyr Leu Lys Asn Asp Phe Ile
                260                 265                 270
Phe Ser Glu Asn Gly Lys Asp Ile Ile Leu Asp Thr Ser Ser Ala Leu
            275                 280                 285
Leu Ser Gln Leu Val His Lys Ile Lys Met Leu Pro Phe Cys His Cys
        290                 295                 300
Leu Met Gln Thr Thr Pro Gln Asp His Ile Val Lys Gln Val Cys Tyr
305                 310                 315                 320
Leu Ile Ala Ser Asn Asn Arg Ile Leu Asp Ala Val Arg Tyr Leu Gln
                325                 330                 335
Thr Ser Val Ile Lys Ser Pro Ile Val Leu Leu Ala Tyr Ala Val
                340                 345                 350
Cys Leu Pro Ala Ala Ile Ile Cys Thr Lys Asn Glu Thr Gln Leu Tyr
            355                 360                 365
Ser His Cys Met Arg Ile Leu Lys Glu Tyr Arg Pro Gly Asp Val Met
        370                 375                 380
Asn Ile Leu His Glu Ser Leu Thr Gln His Leu Asn Lys Cys Pro Ser
385                 390                 395                 400
Ser Thr Cys Ala Tyr Thr Thr Arg Ala Ile Val Gly Thr Lys Ala Asn
                405                 410                 415
Thr Thr Gly Leu Phe Phe Leu Pro Thr Gln
                420                 425

<210> SEQ ID NO 15
<211> LENGTH: 428
<212> TYPE: PRT
<213> ORGANISM: Bovine herpesvirus 4

<400> SEQUENCE: 15

Met Ala Gln Ala Met Leu Thr Met Asp Cys Met Arg Glu Ile Ile Glu
1               5                   10                  15
Asp Leu Ser Ser Asp Ile Asp Ser Phe Ser Gly Gly Glu Ser Ile Asp
                20                  25                  30
Met Glu Ser Glu Leu Glu Glu Gly Glu Ile Glu Ser Asp Thr Asn Ser
            35                  40                  45
Ser Lys Pro Pro Pro Gln Asp Leu Ser Lys Pro Pro Met Met Arg
        50                  55                  60
Ile Pro Arg Lys Arg Val Ala Ser Pro Asp Asn Glu Arg Met Glu Tyr
65                  70                  75                  80
Arg Ser Pro Leu Asn Arg Thr Tyr Pro Pro Phe Thr Glu Arg Tyr
                85                  90                  95
```

-continued

Gly Lys Arg Arg Arg Leu Thr Ala Gly Arg Pro Asn Trp Ser Gly Arg
100 105 110

Val Asn Glu Asp Lys Gly Arg Tyr Arg Arg Arg Gly Leu Ser Asp Asn
115 120 125

Lys Thr Ile Arg His Thr Gln Ala Ser Ile Lys Asp Glu Val Ala Val
130 135 140

Ser Leu Arg Lys Met Lys Ile Pro Thr Gly Met Ile Arg Arg Ala Gly
145 150 155 160

Glu Lys Pro Phe Asp Glu Thr Leu Leu Ser Ser Gly Gly Pro Gly Arg
165 170 175

Tyr Ser Val Phe Leu Pro Arg Ala Pro Glu Phe Lys Leu Glu Arg Tyr
180 185 190

Thr Asp Lys Leu Val Ser Ser Leu Val Glu Lys Gly Gly Glu Asn Gly
195 200 205

Ala Gly Ile Ser Lys Lys Leu Ser His Leu Lys Leu Ser Ser Asn Phe
210 215 220

Ser Val Ile His Ser Phe Leu Asn Lys Ser Ile Asn Tyr His Tyr Trp
225 230 235 240

Val Cys Leu Arg Lys Glu Thr Met Gly Ser Cys Gly Leu Thr Ser Leu
245 250 255

Met Leu Phe Leu Glu Glu Thr Cys Cys Trp Ala Gln Leu Cys Thr Ser
260 265 270

Asn Asp Val Ser Ile Asn Gly Phe Ser Asn Asp Ile Ile Leu Asn Ser
275 280 285

Ala Asn Phe Leu Ser Val Gln Ile Met Phe Lys Leu Arg Ser Leu Val
290 295 300

Met Pro Cys Phe Ala Arg Glu Ala His Asn Ile Ser Leu Val Lys Gln
305 310 315 320

Leu Gly Tyr Leu Val Ser Thr Thr Asn Lys Ile Gln Thr Ala Ala Ser
325 330 335

Leu Ile Arg Glu Leu Lys Leu Asp Thr Lys Leu Cys Leu Leu Ala Ala
340 345 350

Phe Ala Ile Val Val Pro Thr Leu Leu Glu Thr Asp Lys Thr Glu His
355 360 365

Gly Thr Tyr Ala Phe Phe Met Gln Tyr Ile Asn Arg Tyr Arg Pro Gly
370 375 380

Cys Ile Met Ser Leu Tyr Asn Asp Val Ile Ser Ser His Ser Arg Glu
385 390 395 400

Cys Thr Ser Arg Leu Cys Ile Ala Asn Thr Arg Ala Leu Ala Gly Thr
405 410 415

Lys Asp Lys Thr Lys Gly Leu Phe Phe Cys Pro Ile
420 425

<210> SEQ ID NO 16
<211> LENGTH: 436
<212> TYPE: PRT
<213> ORGANISM: Avian herpesvirus 1

<400> SEQUENCE: 16

Met Ala Gln Gln Ala Ile Val Thr Met Ser Ala Leu Arg Arg Thr Met
1 5 10 15

Glu Val Ser Asp Ser Gly Asp Val Ser Ile Asp Ile Ser Ala Glu Asp
20 25 30

Ser Asn Asp Ser Phe His Leu Glu Glu Ser Val Asp Asp Cys Met Asp
35 40 45

-continued

```
Asp Cys Lys Pro Asn Asn Arg Pro Asn Pro Ile Ser Met Lys Pro Ala
 50                  55                  60
Lys Arg Arg Val Phe Met Val Pro Lys Arg Glu Arg Ser Lys Thr Pro
 65                  70                  75                  80
Val Gln His Thr Ser Pro Leu Asn Arg Leu Tyr Pro Asn Val Val Leu
                 85                  90                  95
Gly Lys Gln His Gly Tyr Lys Gln Arg Pro Ala Pro Ser Ala Arg Ser
            100                 105                 110
Arg Arg Pro Gln Pro Tyr Ser Ala Arg Lys Asp Ser Ala Ala Lys Pro
        115                 120                 125
Gln Ser Thr Pro Ser Asn Gln Asn Pro Leu Thr Glu Leu Leu Lys Asn
130                 135                 140
Val Asp Pro Ala Ile Ala Ser Arg Ile Thr Glu Met Arg Ile Pro Arg
145                 150                 155                 160
Ser Met Leu Arg Thr Pro Ser Gly Gln Pro Phe Ala His Trp Leu Met
                165                 170                 175
Pro Ser Ala Glu Asp Ser Ser Lys Phe Ile Asn Val Asn Pro Val Asn
            180                 185                 190
Met Glu Val Glu Glu His Val Asn Val Val Arg Cys Thr Glu
        195                 200                 205
Trp Ala Leu Ile Ser Ser Arg Leu Gln Asp Lys Ser Ile Ser Thr Lys
210                 215                 220
Tyr Leu Ala Glu Asn Phe Tyr Asp Leu Arg Asp Phe Ala Gln Arg Ser
225                 230                 235                 240
Ile Asn Lys Ser Ala Trp Ile Asn Leu Arg Arg Glu Ala Ile Ala Asn
                245                 250                 255
Ala Gly Phe Val Asn Leu Cys Ala Phe Ala Asp Glu Met Met Met Trp
            260                 265                 270
Leu Gln Leu Asn Leu Asn Asn Gln Gly Ser Trp Lys Ala Cys Arg Glu
        275                 280                 285
Asp Ile Ile Leu Thr Gly Ala Pro Asp Met Cys Phe His Ala Leu Gln
290                 295                 300
Lys Val Arg Ala Phe Ile Lys Cys Phe Leu Arg Glu Arg His Gln Arg
305                 310                 315                 320
Ala Leu Val Asn Ala Leu Cys His Ile Ile Cys Phe Glu Gly Gly Ile
                325                 330                 335
Lys Gln Ala Ala Thr Leu Cys Gln Glu Leu Phe Phe Asp Phe Lys Val
            340                 345                 350
Gly Leu Met Val Leu Tyr Phe Leu Thr Pro Tyr Ala Phe Leu Tyr Ser
        355                 360                 365
His Thr Ile Pro Gln Cys Asn Phe Gly Gly Tyr Phe Ser Lys Cys Val
370                 375                 380
Ala Gln Tyr Thr Pro Gly Ala Val Thr Gly Leu Leu Asn Ser Ala Ile
385                 390                 395                 400
Glu Asp His Tyr Lys Asp Cys Thr Ser Gln Asp Cys Thr Asn Leu Ile
                405                 410                 415
Thr Ala Ile Val Ser Pro Glu Thr Ser Asn Lys Gly Leu Leu Phe Phe
            420                 425                 430
Pro Leu Pro Met
        435

<210> SEQ ID NO 17
<211> LENGTH: 409
```

<212> TYPE: PRT
<213> ORGANISM: Murineherpesvirus68

<400> SEQUENCE: 17

```
Met Ala Gln Gln Met Leu Glu Ala Gly Ala Leu Asp Gln Met Met Glu
1               5                   10                  15

Gly Leu Pro Ser Asp Phe Asp Phe Asp Thr Ser Asp Glu Glu Gly Glu
            20                  25                  30

Leu Ser Asp Ser Pro Pro Val Glu Glu Pro Thr Gly Pro Val Arg Asp
        35                  40                  45

Val Val Tyr Glu Pro Asp Pro Leu Phe Asp Asp Pro Pro Thr Pro
    50                  55                  60

Ser Pro Asp Val Lys Pro Pro Ser Pro Lys Ala Arg Lys Arg Ala Leu
65                  70                  75                  80

Ser Pro Glu Ile Val His Asn Ser Pro Leu Leu Arg Asp Thr Thr Lys
                85                  90                  95

Tyr Glu Pro Ala Pro Lys Arg Ser Tyr Ser Tyr His Pro Arg Arg Ser
            100                 105                 110

Pro Gln Arg Glu Asn Ala Asn Gln Lys Gln Lys Arg Gly Pro Asp Ser
        115                 120                 125

Arg Arg Pro Asn Arg Trp Asn Gln Lys Ser Gln Lys Gln Tyr Trp Ser
130                 135                 140

Pro Lys Pro Leu Leu Asp Tyr Ser Lys Ile Pro Arg Ala Glu Tyr Lys
145                 150                 155                 160

Asn Ala Lys Leu Leu Val Pro Thr Thr Gly Lys Leu Arg Pro Glu Phe
                165                 170                 175

Tyr Thr Asp Arg Phe Val Asp Ala Ile Ile Gln Asn Ala Ala Arg Asn
            180                 185                 190

Cys Pro Val Ser Glu Lys Ala Val Ser Leu Lys Asn Ile Glu Glu Ser
        195                 200                 205

Phe Lys Leu Leu Asn Ser Phe Phe Asn Ser Gly Ile Asn Lys Asp His
210                 215                 220

Trp Leu Ser Thr Arg Tyr Phe Ala Ile Phe Asn Asn Gly Leu Val Val
225                 230                 235                 240

Leu Thr His Met Leu Asp Glu Gln Leu Ala Trp Ala Tyr Ala Cys Leu
                245                 250                 255

Lys His Gly Arg Glu Leu Pro Thr Asp Asp Ile Leu Met Ser Thr Ser
            260                 265                 270

Glu Lys Leu Ser Gln Gln Leu Val Ile Lys Leu Ile Glu Val Ile Lys
        275                 280                 285

Cys Ile Glu Lys Asp Gly Ile Phe Ser Arg Ile Leu Lys Gly Val Ala
290                 295                 300

Asp Ala Val Cys Leu Lys Ala Gln Phe Leu Arg Gly Met Ile Thr Leu
305                 310                 315                 320

Lys Arg Thr Pro Cys Ser Leu Pro Met Tyr Thr Leu Phe Val Tyr Val
                325                 330                 335

Leu Thr Ile Pro Thr Leu Arg Thr Arg Val Ile Arg Asp Pro Leu Leu
            340                 345                 350

Thr Gln Cys Lys Asp Val Val Leu Lys Tyr Gln Pro Gly Asp Cys Ile
        355                 360                 365

Thr Leu Leu Lys Ala Ala Leu Asn Cys His Gln Cys Asn Lys Asp Cys
370                 375                 380

Asp Lys Cys Lys Tyr Ile Leu Asp Pro Leu Leu Gly Gln Thr His Arg
385                 390                 395                 400
```

```
Thr Lys Gly Val Phe Phe Val Cys Glu
            405

<210> SEQ ID NO 18
<211> LENGTH: 479
<212> TYPE: PRT
<213> ORGANISM: Epstein-Barr virus

<400> SEQUENCE: 18

Met Val Pro Ser Gln Arg Leu Ser Arg Thr Ser Ile Ser Ser Asn
1               5                  10                  15

Glu Asp Pro Ala Glu Ser His Ile Leu Glu Leu Glu Ala Val Ser Asp
                20                  25                  30

Thr Asn Thr Asp Cys Asp Leu Asp Pro Met Glu Gly Ser Glu Glu His
            35                  40                  45

Ser Thr Asp Gly Glu Ile Ser Ser Ser Glu Glu Glu Asp Glu Asp Pro
    50                  55                  60

Thr Pro Ala His Ala Ile Pro Ala Arg Pro Ser Ser Val Val Ile Thr
65              70                  75                  80

Pro Thr Ser Ala Ser Phe Val Ile Pro Arg Lys Lys Trp Asp Leu Gln
                85                  90                  95

Asp Lys Thr Val Thr Leu His Arg Ser Pro Leu Cys Arg Asp Glu Asp
                100                 105                 110

Glu Lys Glu Glu Thr Gly Asn Ser Ser Tyr Thr Arg Gly His Lys Arg
            115                 120                 125

Arg Arg Gly Glu Val His Gly Cys Thr Asp Glu Ser Tyr Gly Lys Arg
    130                 135                 140

Arg His Leu Pro Pro Gly Ala Arg Ala Pro Arg Ala Pro Arg Ala Pro
145             150                 155                 160

Arg Val Pro Arg Ala Pro Arg Ser Pro Arg Ala Pro Arg Ser Asn Arg
                165                 170                 175

Ala Thr Arg Gly Pro Arg Ser Glu Ser Arg Gly Ala Gly Arg Ser Thr
            180                 185                 190

Arg Lys Gln Ala Arg Gln Glu Arg Ser Gln Arg Pro Leu Pro Asn Lys
    195                 200                 205

Pro Trp Phe Asp Met Ser Leu Val Lys Pro Val Ser Lys Ile Thr Phe
210                 215                 220

Val Thr Leu Pro Ser Pro Leu Ala Ser Leu Thr Leu Glu Pro Ile Gln
225                 230                 235                 240

Asp Pro Phe Leu Gln Ser Met Leu Ala Val Ala Ala His Pro Glu Ile
                245                 250                 255

Gly Ala Trp Gln Lys Val Gln Pro Arg His Glu Leu Arg Arg Ser Tyr
            260                 265                 270

Lys Thr Leu Arg Glu Phe Phe Thr Lys Ser Thr Asn Lys Asp Thr Trp
    275                 280                 285

Leu Asp Ala Arg Met Gln Ala Ile Gln Asn Ala Gly Leu Cys Thr Leu
290                 295                 300

Val Ala Met Leu Glu Glu Thr Ile Phe Trp Leu Gln Glu Ile Thr Tyr
305                 310                 315                 320

His Gly Asp Leu Pro Leu Ala Pro Ala Glu Asp Ile Leu Leu Ala Cys
                325                 330                 335

Ala Met Ser Leu Ser Lys Val Ile Leu Thr Lys Leu Lys Glu Leu Ala
            340                 345                 350

Pro Cys Phe Leu Pro Asn Thr Arg Asp Tyr Asn Phe Val Lys Gln Leu
```

-continued

```
                355                 360                 365
Phe Tyr Ile Thr Cys Ala Thr Ala Arg Gln Asn Lys Val Val Glu Thr
    370                 375                 380

Leu Ser Ser Ser Tyr Val Lys Gln Pro Leu Cys Leu Leu Ala Ala Tyr
385                 390                 395                 400

Ala Ala Val Ala Pro Ala Tyr Ile Asn Ala Asn Cys Arg Arg Arg His
                405                 410                 415

Asp Glu Val Glu Phe Leu Gly His Tyr Ile Lys Asn Tyr Asn Pro Gly
                420                 425                 430

Thr Leu Ser Ser Leu Leu Thr Glu Ala Val Glu Thr His Thr Arg Asp
                435                 440                 445

Cys Arg Ser Ala Ser Cys Ser Arg Leu Val Arg Ala Ile Leu Ser Pro
        450                 455                 460

Gly Thr Gly Ser Leu Gly Leu Phe Phe Val Pro Gly Leu Asn Gln
465                 470                 475
```